(12) United States Patent
Drevik et al.

(10) Patent No.: US 8,551,063 B2
(45) Date of Patent: Oct. 8, 2013

(54) ABSORBENT ARTICLE

(75) Inventors: Solgun Drevik, Mölnlycke (SE);
Chatrine Stridfeldt, Hovås (SE);
Magnus Melander, Göteborg (SE)

(73) Assignee: SCA Hygiene Products AB, Göteborg (SE)

( * ) Notice: Subject to any disclaimer, the term of this patent is extended or adjusted under 35 U.S.C. 154(b) by 343 days.

(21) Appl. No.: 12/934,121

(22) PCT Filed: Apr. 24, 2008

(86) PCT No.: PCT/SE2008/050471
§ 371 (c)(1),
(2), (4) Date: Sep. 23, 2010

(87) PCT Pub. No.: WO2009/133504
PCT Pub. Date: Oct. 29, 2009

(65) Prior Publication Data
US 2011/0046595 A1    Feb. 24, 2011

(51) Int. Cl.
*A61F 13/15* (2006.01)
(52) U.S. Cl.
USPC ............ 604/385.02; 604/385.03; 604/385.04; 604/385.201
(58) Field of Classification Search
USPC .................. 604/385.02–385.06, 385.201
See application file for complete search history.

(56) References Cited

U.S. PATENT DOCUMENTS

| | | | |
|---|---|---|---|
| 4,608,047 A | 8/1986 | Mattingly | |
| 4,781,712 A | 11/1988 | Barabino et al. | |
| 4,917,675 A * | 4/1990 | Taylor et al. | 604/385.02 |
| 5,088,993 A | 2/1992 | Gaur | |
| 5,478,336 A | 12/1995 | Pigneul | |
| 5,769,837 A | 6/1998 | Parr | |
| 5,993,430 A * | 11/1999 | Gossens et al. | 604/385.02 |
| 2004/0073185 A1 | 4/2004 | Ichiura et al. | |
| 2005/0137555 A1* | 6/2005 | Mizutani et al. | 604/385.02 |
| 2007/0250030 A1 | 10/2007 | Woltman et al. | |

FOREIGN PATENT DOCUMENTS

| | | |
|---|---|---|
| CN | 1284849 A | 2/2001 |
| DE | 4 127 411 C1 | 10/1992 |
| EP | 0 314 535 A1 | 5/1989 |
| EP | 0 471 385 A1 | 2/1992 |
| EP | 0 625 345 A1 | 11/1994 |
| EP | 0 668 067 | 8/1995 |
| EP | 1 407 747 | 4/2004 |

(Continued)

OTHER PUBLICATIONS

Office Action (Notice of Reasons for Rejection) dated Sep. 25, 2012, issued in corresponding Japanese Patent Application No. 2011-506225, and an English Translation thereof. (4 pages).

(Continued)

*Primary Examiner* — Lynne Anderson
(74) *Attorney, Agent, or Firm* — Buchanan Ingersoll & Rooney PC

(57) ABSTRACT

The backsheet of an absorbent body is used as a wrapper. The backsheet includes a fastening device intended for use in an undergarment. The absorbent article is folded into a packet in such a way that the fastening device on the backsheet becomes hidden within the packet.

31 Claims, 28 Drawing Sheets

(56) References Cited

FOREIGN PATENT DOCUMENTS

| GB | 2 380 138 | 4/2003 |
|----|-----------|--------|
| JP | H02-501278 A | 5/1990 |
| JP | 2004-148102 A | 5/2004 |
| JP | 2007-029351 A | 2/2007 |
| WO | WO 99/32059 A1 | 7/1999 |
| WO | WO 99/52483 A1 | 10/1999 |

OTHER PUBLICATIONS

Office Action dated Jun. 1, 2012, issued in corresponding Thailand Patent Application No. 0901001625, and an English Translation thereof. (5 pages).

International Search Report (PCT/ISA/210) issued on Jan. 15, 2009, by Swedish Patent Office as the International Searching Authority for International Application No. PCT/SE2008/050471.

Written Opinion (PCT/ISA/237) issued on Jan. 15, 2009, by Swedish Patent Office as the International Searching Authority for International Application No. PCT/SE2008/050471.

Written Opinion (PCT/IPEA/408) issued on Jul. 2, 2010, by Swedish Patent Office as the International Preliminary Examining Authority for International Application No. PCT/SE2008/050471.

Office Action (Notification of the First Office Action) dated Dec. 14, 2013, issued in corresponding Chinese Patent Application No. 200880128798.0, and an English Translation thereof. (10 pages).

Search Report issued in corresponding European Patent Application No. 08779272.7, dated Apr. 17, 2013.

\* cited by examiner

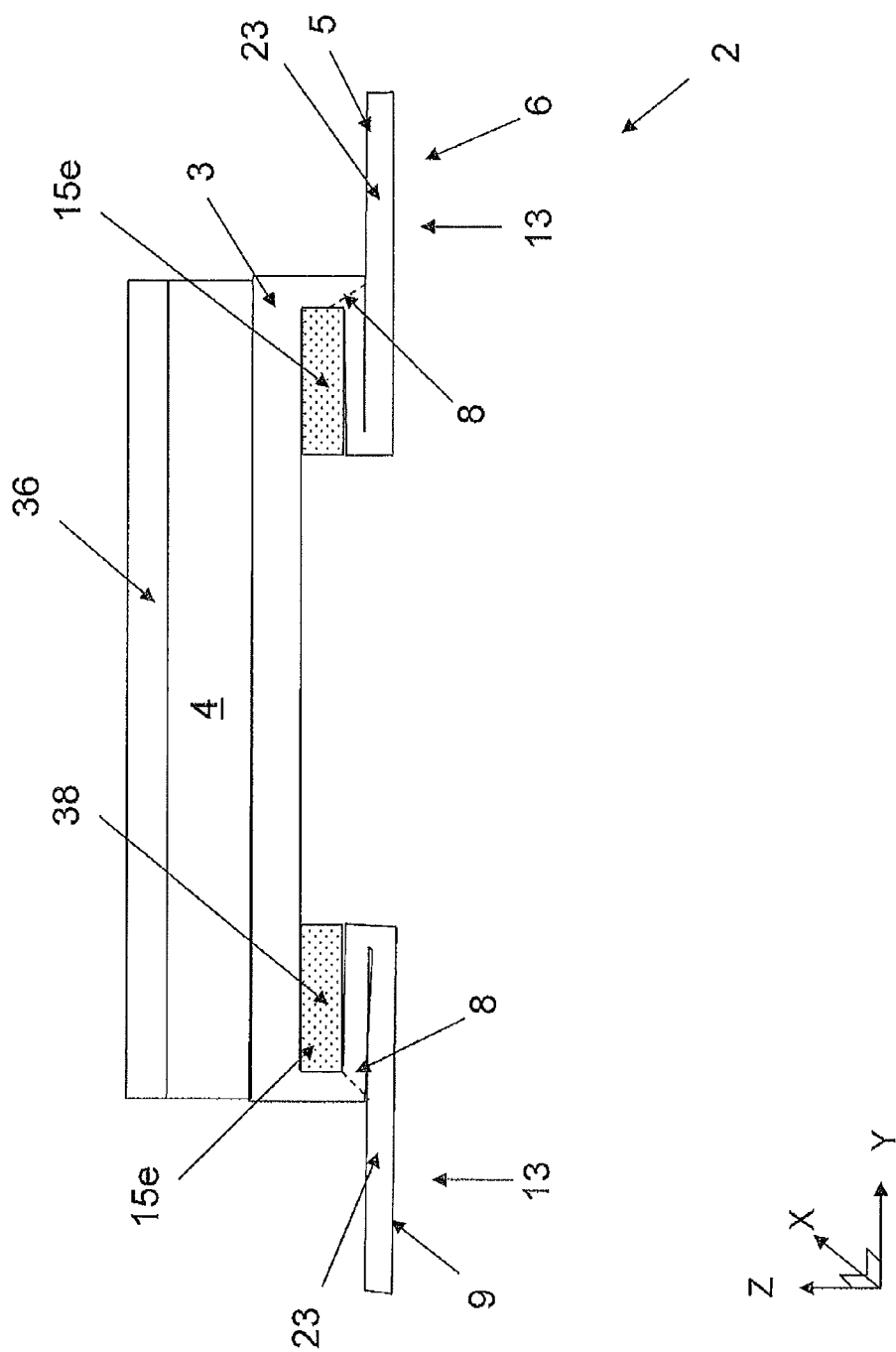

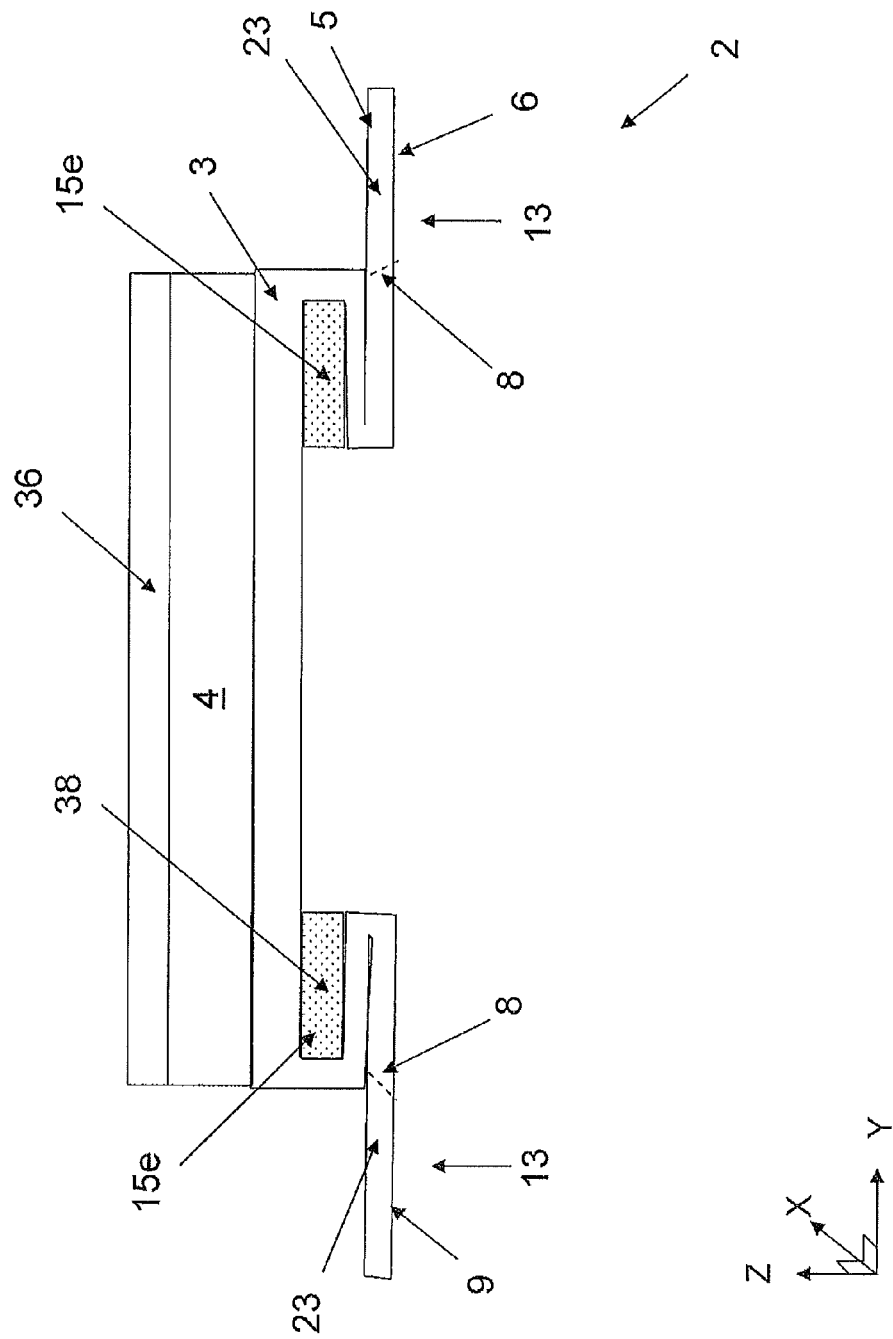

ABSORBENT ARTICLE

TECHNICAL FIELD

The present invention relates to a packet for an absorbent article according to the preamble of claim 1.

BACKGROUND ART

In the field of absorbent articles such as sanitary napkins, panty liners and light incontinence protection liners, it is known to fold the absorbent article into a small packet that is discrete and easy for a user to store and carry.

WO 99/52483 teaches a packet for an absorbent article. The packet comprises a wrapper that encloses a folded absorbent article. The packet is opened by removal of tear tabs from the wrapper. After the tear tabs have been removed, the absorbent article is unveiled by removing and tossing away the wrapper.

One problem with the packet according to prior art is that the wrapper has to be disposed. One part of the problem lies in that the user has to either store the wrapper or to find a suitable waste bin. Another part of the problem is that the wrapper, even if disposed properly, adds to the problem of waste management, which is both costly and may affect the environment negatively.

Hence, there exists a need for a packet for an absorbent article with reduced waste products.

DISCLOSURE OF INVENTION

The invention intends to remedy the above problems by introduction of a packet for an absorbent article according to the appended claims.

The invention relates to an absorbent article comprising a backsheet and an absorbent article. The backsheet has an outside and an inside and comprises two longitudinally extending edge portions. Here "longitudinally extending edge portions" refers to the absorbent article in an unfolded state. When the absorbent article is folded into a packet "longitudinally extending" refers to a direction coinciding with the general direction of the longitudinally extending edge portions in the folded absorbent article.

The absorbent article comprises fastening means positioned on the outside of the backsheet for fastening in an undergarment when the absorbent article is in an unfolded position.

The absorbent body is positioned on the inside of the backsheet and the absorbent article is folded into the packet in such a way that the absorbent body is protected by the backsheet. The absorbent article is in the folded position folded into a packet in such a way that at least a part of the outside of the backsheet makes up an exterior surface of the packet and in such a way that the fastening means is positioned inside the packet and in such a way that each longitudinally extending edge portion is folded over itself at least once and attached to itself forming openable or removable first sealed portions for sealing longitudinally extending side portions of the packet. Here "longitudinally extending side portions of the packet" means at least a part of the longitudinally extending edge portions of the backsheet, but could also comprise the entire longitudinally extending edge portions of the backsheet.

One benefit of the invention is that the amount of waste products is minimized since the integrated wrapper in the form of the backsheet replaces the previously used separate wrapper.

The fastening means comprises an attachment surface facing away from the outside of the absorbent article when the absorbent article is in the unfolded position. The attachment surface is arranged for attachment in the undergarment when the absorbent article is in the unfolded position. According to the invention the absorbent article is folded in such a way that the attachment surface is in contact only with the outside of the backsheet when the absorbent article is in the folded position, i.e. when a packet has been formed.

One benefit of the invention is that the fastening means can be used both for attachment in the undergarment and as sealing means and attachment means for sealing and forming the packet.

In one embodiment of the invention, the first sealed portions comprise first sealing means for sealing the first sealed portions. The first sealed portions comprise first tearing lines for separation of first tear tabs, comprising the first sealing means, from the packet when the absorbent article is in its folded position for opening the packet. In another embodiment, the first sealed portions comprises openable first sealing means, for example in the form of the fastening means, wherein the first sealed portions are separable for opening the packet without removing any first tear tabs.

In one embodiment of the invention, the longitudinally extending edge portions are folded over longitudinally extending folding lines for forming the first sealed portions. The fastening means may then be positioned on the outside of the backsheet on the folded longitudinally extending edge portions.

According to the invention, the fastening means is positioned inside the packet in such a way that the fastening means is in contact only with the outside of the backsheet when the absorbent article is in the folded position.

The fastening means may be arranged to seal a laterally extending side portion of the packet in a folded position thereby forming openable second sealed portions.

The backsheet may comprise two laterally extending edge portions being folded over each other forming a third sealed portion for sealing the laterally extending side portion of the packet The third sealed portion may comprise second tearing lines for separation of a second tear tab from the backsheet from the packet when the absorbent article is in its folded position. However, the third sealed portions may be separable, for opening the packet, instead of removing the second tear tab.

The backsheet may comprise fastening flaps extending, when the absorbent article is in the unfolded position, along each of the longitudinally extending edge portions and extending in the lateral direction in a direction away from the absorbent body.

The absorbent article advantageously comprises biodegradable materials or renewable resource materials or products having their origin in a renewable or biodegradable material that will not cause environmental problems as waste products. Examples of such products are: protein based products such as gluten, soya and gelatine; viscose; biodegradable polymers such as Poly Capro Lactone (PCL), Poly Hydroxy-lAlkonoate (PHA), Poly Lactide Acid (PLA), and Poly Hydroxy Butyrate (PHB); and starch based products, such as bamboo, cellulose, wood pulp and cotton; and polyolefin such as PolyEthylene (PE) and PolyPropylene (PP) based on renewable resource materials. Hence, the absorbent article may partly or fully be made from renewable resource materials that may be biodegradable.

BRIEF DESCRIPTION OF DRAWINGS

The invention will be described below in connection to a number of drawings, in which:

FIG. 27 schematically shows a side view of an absorbent article according to a seventh embodiment of the invention, and in which;

FIG. 28 schematically shows a side view of an absorbent article according to an eight embodiment of the invention.

EMBODIMENT(S) OF THE INVENTION

Figure 1:
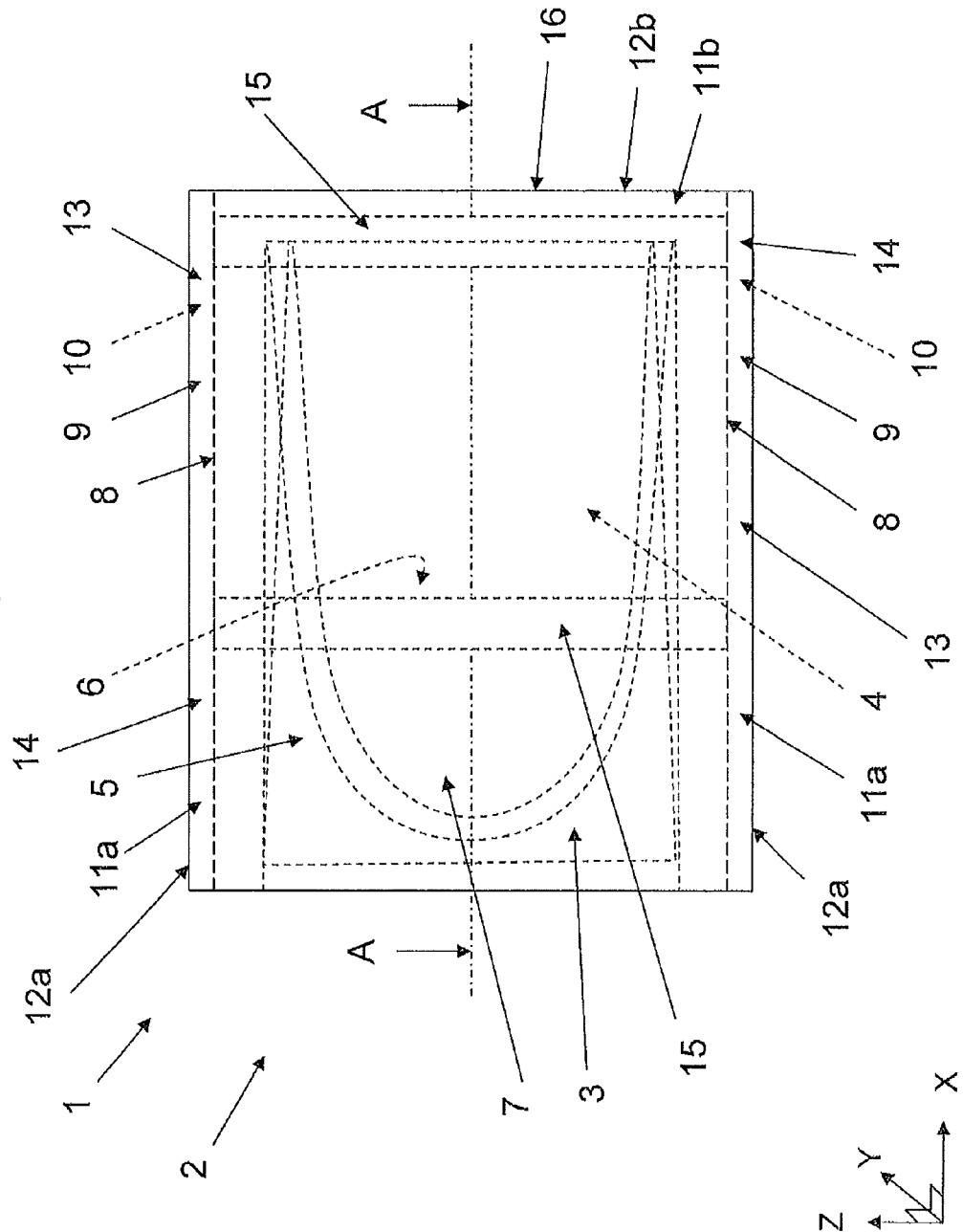
FIG. 1 schematically shows a packet for an absorbent article according to the invention.

FIG. 1 schematically shows a packet 1 for an absorbent article according to the invention. The packet comprises an absorbent article 2 comprising a backsheet 3 and an absorbent body 4. The backsheet 3 has an outside 5 and inside 6 and the inside of the backsheet 3 is directly attached to the absorbent body 4 and it is normally not possible to separate the backsheet 3 from the absorbent body 4 without destroying the absorbent article 2. In order to explain the invention in a simple way, the absorbent article 2 is described in connection to FIGS. 1-16 as being constituted only by the backsheet 3 and the absorbent body 4, but the absorbent body 4 may comprise a number of layers of different materials, for example a hydrophobic or hydrophilic topsheet, liquid distribution layers, super absorbents, and absorbent materials with various absorbent abilities. Furthermore, the backsheet 3 may comprise different layers or may have different properties in different zones, but the backsheet 3 is characterized in that it is liquid impermeable.

The absorbent article 2 is folded in such a way that at least a part of the backsheet 3 constitutes an exterior surface of the packet 1. The absorbent article 2 may be folded in a number of different configurations, but common for all embodiments are that the backsheet 3 constitutes a wrapper 7 for the packet 1. Dependent on how the absorbent article 2 is folded, the entire backsheet 3 may constitute the wrapper 7 or only a part of the backsheet may constitute the wrapper 7.

FIG. 1 shows that the packet 1 comprises two first tearing lines 8 intended to be used for separation of two sections in the form of first tear tabs 9 of the backsheet 3 from the packet 1. The first tear tabs 9 comprise first sealing means 10 for bonding together those parts of the backsheet 3 that is present in the first tear tabs 9. The separation of the first tear tabs 9 removes the first sealing means 10 and makes it possible to un-wrap the packet 1, i.e. makes it possible to unfold the absorbent article 2. In FIG. 1 the first tearing lines 8 are straight, but they may have a curved shape. The first tear tabs 9 are position along longitudinally extending X side portions 11a of the packet. Here, "longitudinally extending side portion" means a portion of the packet including a longitudinally extending side edge 12a of the packet 1 wherein the side edge 12a delimits the packet 1 in the lateral direction. The backsheet 3 comprises longitudinally extending edge portions 13 delimited by the first tearing lines 8 and arranged to form the first tear tabs 9 when the absorbent article has been folded into the packet 1. The first sealing means 10 are comprised in longitudinally extending first sealed portions 14 intended to be removed by the first tear tabs 9.

The first tearing lines 8 may be in the form of perforations in the backsheet 3, but may also be arranged in the form of weakened parts. The first tearing lines 8 may also be arranged in the backsheet 3 by introduction of tearing threads that are integrated in the backsheet for separation or breaking of the material in the backsheet 3 when the tearing threads are pulled away from the backsheet 3.

The first sealing means 10 may comprise an adhesive such as glue or any other suitable adhesive. The first sealing means 10 may be in the form of seams being created by any type of welding, for example ultrasonic welding, laser welding or heat welding. The seams may also be created by any type of mechanical machining, for example embossing or another type of machining where pressure is applied on the first tear tabs 9 of the backsheet 3 that forms the seams.

In FIG. 1, the absorbent article 2 Comprises fastening means 15 positioned on the outside of the backsheet for sealing laterally extending Y side portions 11b of the packet 1 in such a way that a second sealed portion 16 is formed.

Figure 2:
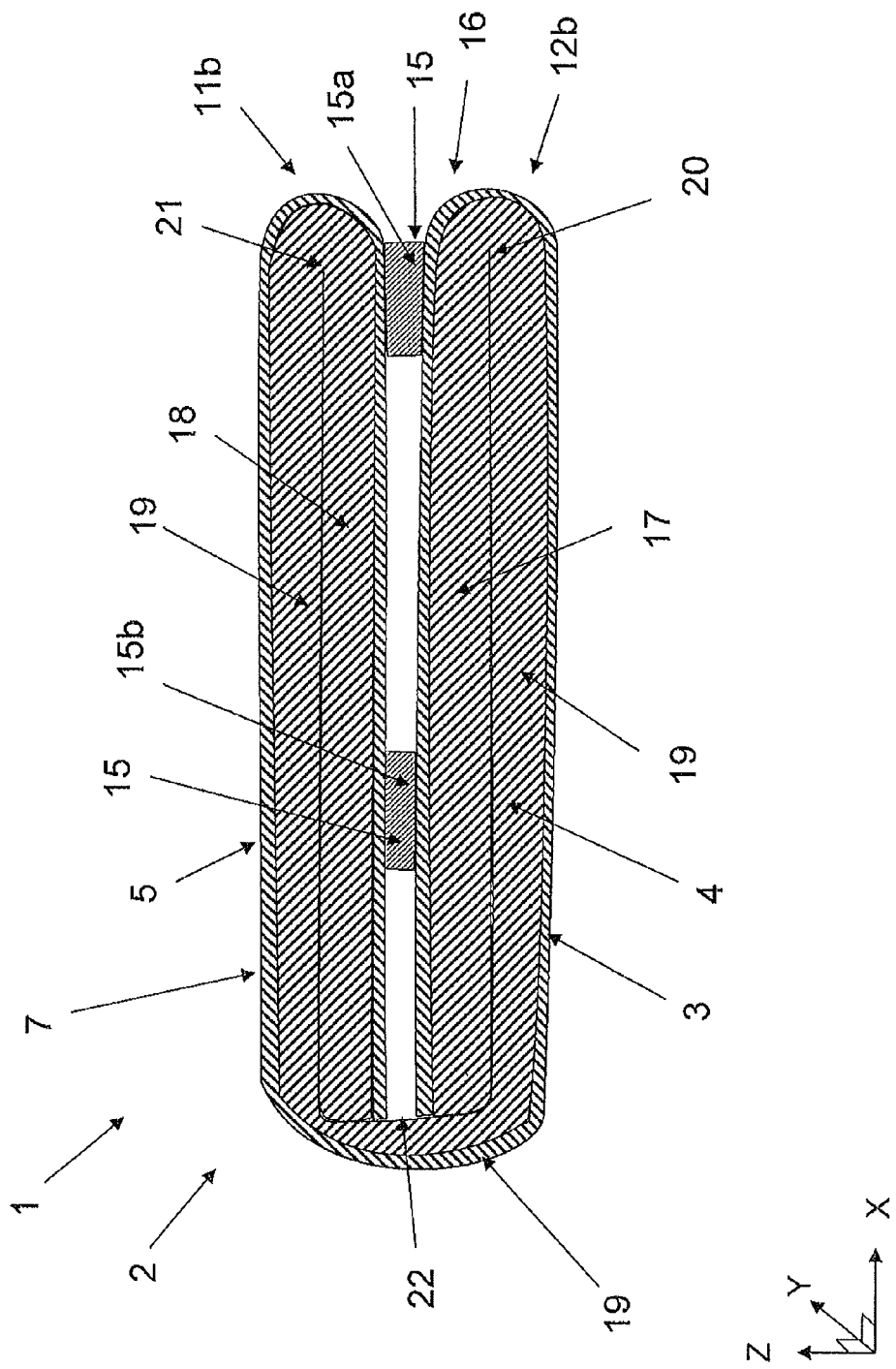
FIG. 2 schematically shows a cross-section along a line A-A in FIG. 1 according to a first embodiment of the invention.

FIG. 2 schematically shows a cross-section along a line A-A in FIG. 1 according to a first embodiment of the invention. The absorbent article 2 has an extension in the longitudinal direction X and an extension in the lateral direction Y being essentially perpendicular to the longitudinal direction X. The absorbent article 2 comprises, in the longitudinal direction X, a front portion 17, a rear portion 18 and a central portion 19 therebetween. The division into portions is only for aid in describing the invention and the size of the portions may thus vary.

FIG. 2 shows that the front portion 17 is folded over a first folding line 20 and over half the central portion 19 and that the rear portion is folded over a second folding line 21 and the other half of the central portion 19. Hence, in this embodiment the front portion 17 and the rear portion 18 each constitute ¼ of the absorbent article 2 in the longitudinal direction X and the central portion 19 constitute 2/4 of the absorbent article 2 in the longitudinal direction X. The absorbent article 2 is also folded over a third folding line 22 being positioned in the middle of the central portion 19 such that the front portion 17 and the rear portion 18 face each other. The absorbent article 2 is thus folded in such a way that the backsheet 3 in the rear portion 18 faces the backsheet 3 in the front portion 17. This means that the absorbent body 4 in the front portion 17 faces, or lies against, the absorbent body 4 in a part of the central portion 19 and that the absorbent body 4 in the rear portion 18 faces, or lies against, the absorbent body 4 in another part of the central portion 19.

FIG. 2 shows that only a part of the backsheet 3 constitutes the wrapper 7. In this embodiment it is the backsheet 3 of the central portion 19 that constitutes the wrapper 7. With reference to FIG. 1, in the embodiment shown in FIG. 2 the first tear tabs 9 that are used for sealing the packet 1 must comprise backsheet 3 material at least from the central portion 19 in order to seal the packet 1 properly, but may also comprise backsheet 3 material from the front portion 17 and/or the rear portion 18.

FIG. 2 shows that the fastening means 15 are positioned on the opposite side of the backsheet 3 with reference to the absorbent body. In FIG. 1 the fastening means comprises first fastening means 15a and second fastening means 15b. The first fastening means 15a is positioned in the front portion 17 and the second fastening means 15b in the rear portion 18 for sealing the packet 1 when the absorbent article 2 has been folded into the packet 1 according to the above. The first fastening means 15a may be positioned adjacent the first folding line 20 and the second fastening means 15b may be positioned adjacent the second folding line 21 with an extension in the lateral direction for sealing the packet 1 in the second sealed portion 16. However, the invention is not limited to a first and a second fastening means 15b according, but the fastening means 15 may comprise only the first fastening means 15a or the second fastening means 15b or additional fastening means. FIG. 2 shows at least two fastening means being used, but only one, in FIG. 2 the first fastening means 15a, is positioned for sealing the packet 1 in the lateral direction adjacent a folding line, in FIG. 2 the first folding line 20. The second fastening means 15b is positioned at a farther distance from the second folding line 21 for sealing the packet 1 at a different position relative the first fastening means 15a thereby giving double safety against contamination of the absorbent body 4 from the outside of the packet.

Hence, at least one fastening means 15 advantageously has a lateral extension from one longitudinally extending side of the absorbent article 2 to the other side of the absorbent article 2 in order to enable a proper sealing of the packet 1 in the second sealed portion 16 so that dirt, water and other substances are hindered from entering the packet. Additional fastening means 15 may be arranged between the first/second folding line 21 and the third folding line 22 in order to further seal the packet 1 and also to aid in forming the packet 1 geometry.

The second sealed portion 16 of the packet may coincide with the laterally extending side portion 11b of the packet 1 or may be arranged partly within the laterally extending side portion 11b or at a distance from the laterally extending side portion 11b. Here, "laterally extending side portion" means a portion of the packet including a laterally extending side edge 12b of the packet 1 wherein the laterally extending side edge 12b delimits the packet 1 in the longitudinal direction.

The fastening means 15 may be of a kind that separates into two parts when being subject to external force. Here, "separates" refers to when the fastening means 15 adhere more to the backsheet than to itself. This means that when the packet 1 is opened and force is applied to the fastening means, via the backsheet 3 in the front portion 17 and the rear portion 18 respectively, the internal forces, i.e. cohesion forces in the fastening means 15 is less than the adhesion force to the backsheet 3. One advantage of using such separable fastening means 15 is that, upon opening of the packet, each fastening means 15 is split into two fastening means 15, one on each side of the opened portions. The newly formed two fastening means 15 can then be used for attachment in an undergarment when the absorbent article 2 is used.

The fastening means 15 may also be arranged to have two attachment surfaces with different adhesive forces so that upon opening of the packet, the fastening means 15 releases from one backsheet surface, for example in the front portion 17, but continues to stick to another backsheet surface, for example in the rear portion 18. Furthermore, the fastening means may in the form of an adhesive have different bonding properties in different zones and may have different adherent properties.

The fastening means 15 may be applied in the front portion 17 of the backsheet 3 and/or the rear portion 18 of the backsheet 3 such that the fastening means 15 adhere to the backsheet 3 of the opposing part upon forming the packet 1.

Another possibility is to apply one part of the fastening means 15 on the front portion 17 of the backsheet 3 and an opposing part on the rear portion 18 of the backsheet. The two parts of the fastening means 15 are then brought together when the packet 1 is formed in order to create the seal. In the above embodiments regarding the fastening means 15, the fastening means 15 may be a mechanical fastening means 15, for example of hook and loop type, or may be an adhesive such as glue.

Furthermore, a hump or elevated portion (not shown) may be positioned in the central portion and/or in parts of the front or rear portion. The third folding line and the folding of the absorbent article may aid in shaping the hump for use against the genital area of a user.

Figure 3:
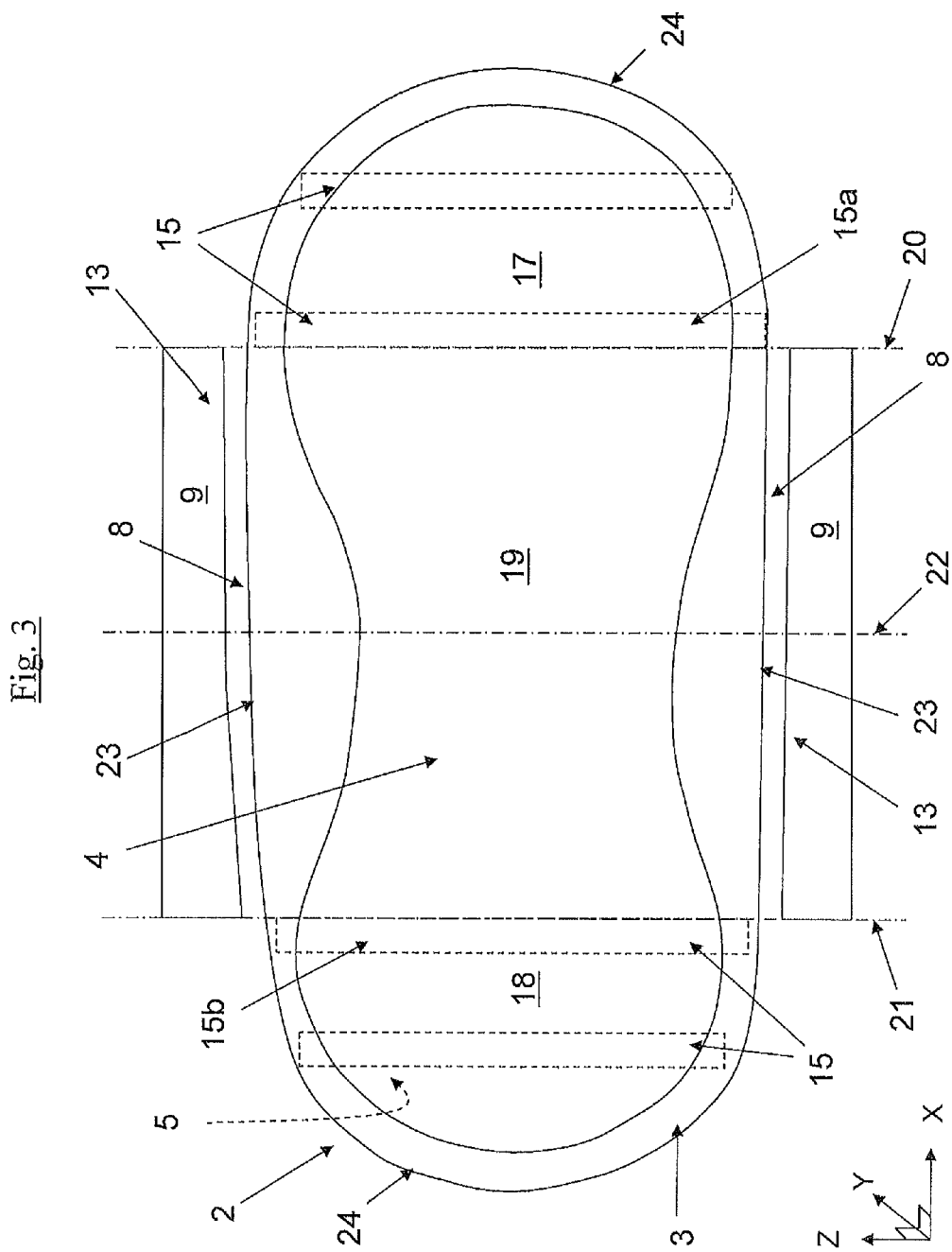
FIG. 3 schematically shows a first example of the packet in FIG. 2, in an unfolded position.

FIG. 3 schematically shows a first example of the packet 1 in FIG. 2, in an unfolded position. FIG. 3 shows that the backsheet 3 comprises extra backsheet material in the longitudinally extending edge portions 13 only in the central portion for forming of the first tear tabs 9. FIG. 3 shows that the first tear tabs 9 have been separated from the absorbent article 2 along the first tearing lines 8 and that the absorbent article 2 has been unfolded. It should be noted that the first tear tabs 9 may comprise backsheet 3 material also in the front portion 17 and/or in the rear portion 18, but that the first tear tabs 9 must be positioned at least in the central portion 19 when the absorbent article 2 is folded in the manner described in connection to FIG. 2.

FIG. 3 shows longitudinally extending edges 23 and laterally extending edges 24 delimiting the backsheet 3. At least a part of the longitudinally extending edges 23 are created when the first tear tabs 9 are torn away from the packet 1. Hence, the first tearing lines 8 coincide with the longitudinally extending edges 23 when the packet 1 is sealed, i.e. when the first tear tabs 9 have not been torn away. The position of the first tearing lines 8 thus forms the shape of the absorbent article when the first tear tabs 9 are torn away. The longitudinally extending edges 23 extend on either side of the absorbent article 2 from the laterally extending edge 24 in the rear portion 18 to the laterally extending edge 24 in the front portion 17. The longitudinally extending edges 23 are in FIG. 3 essentially straight, but may be curved or undulated. The laterally extending edges 24 may be curved in a half circular shape, but may be formed with another shape, for example straight or undulating.

In FIG. 3 it is shown that the absorbent body 4 has a different shape than the backsheet 3 when the first tear tabs 9 are torn away. However, the absorbent body 4 may have the same contour as the laterally and longitudinally extending edges 23, i.e. may have the same shape as the backsheet 3. In FIG. 3 the absorbent body 4 is hour-glass shaped, but may have any other suitable form, for example square, rectangular, oval, round, triangular, or pentagonal.

FIG. 3 shows that the first and second fastening means 15a and 15b in FIG. 2 have been split into four fastening means 15 arranged on the backsheet 3 for attachment in an undergarment. In FIG. 3, the fastening means 15 are straight and have lateral extensions from one longitudinally extending edge 23 to the other longitudinally extending edge 23. However, the fastening means 15 adjacent the first and second folding lines 20, 21 may have a different extension than the fastening means 15 positioned in the rear portion 18 and the front portion 17. It is advantageous if the fastening means 15 adjacent the first and second folding lines 20, 21 have an extension between the longitudinally extending edges 23, i.e. between the first sealing means 10, because the fastening means 15 then seals the packet 1 together with the first sealing means 10 when the absorbent article 2 is folded according to FIG. 2. Furthermore, the fastening means 15 may be straight, curved, dotted, broken, etc. as long as the packet becomes sealed.

Figure 4:
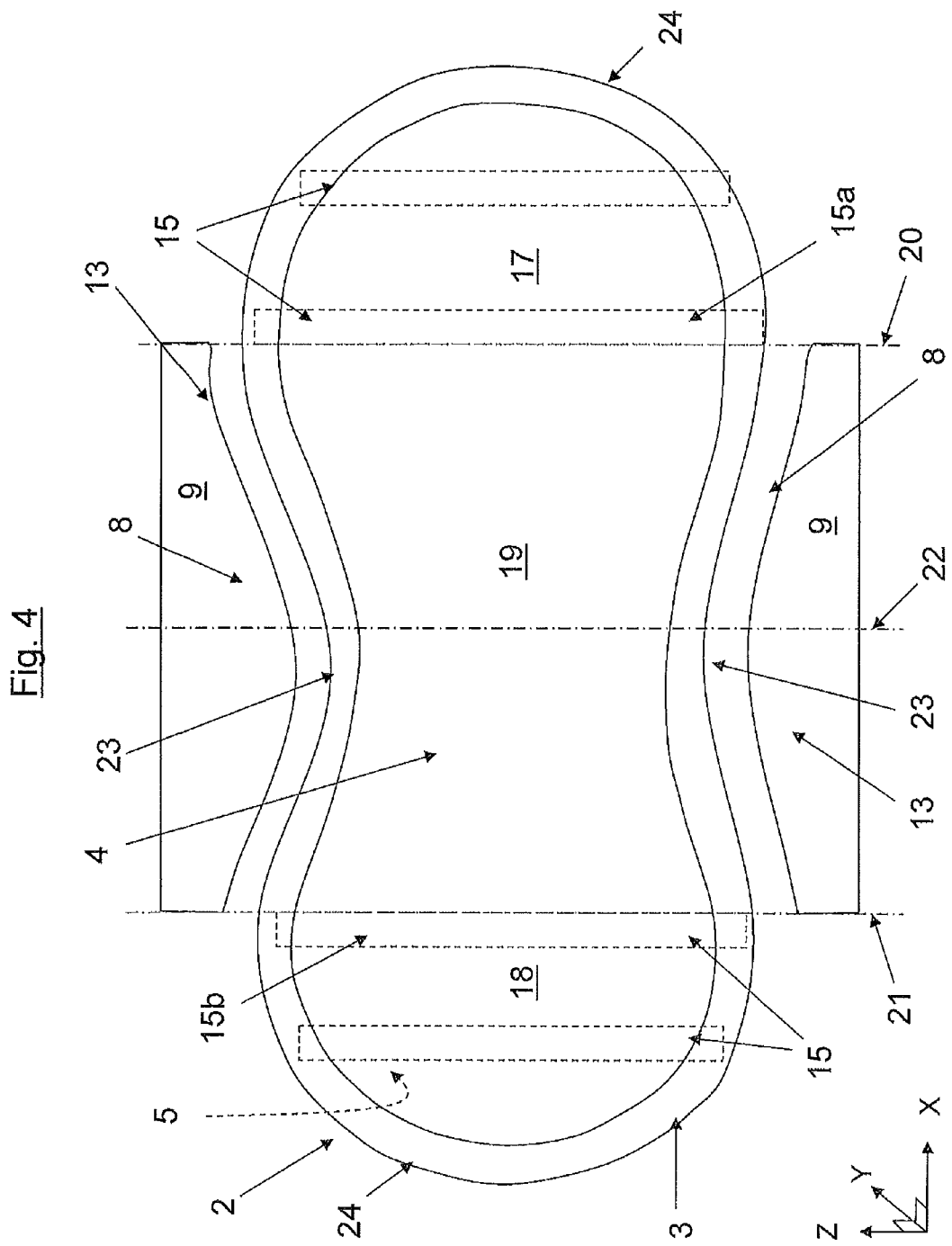
FIG. 4 schematically shows a second example of the packet in FIG. 2, in an unfolded position.

FIG. 4 schematically shows a second example of the packet 1 in FIG. 2, in an unfolded position. FIG. 4 differs from FIG. 2 only in that the longitudinally extending edges 23, hence also the first tearing lines 8, are curved so that the backsheet 3 and the absorbent body 4 has the same contour. In FIG. 4 the contour is in the form of an hour-glass, but other shapes are possible according to what has been described in connection to FIG. 3.

Figure 5:
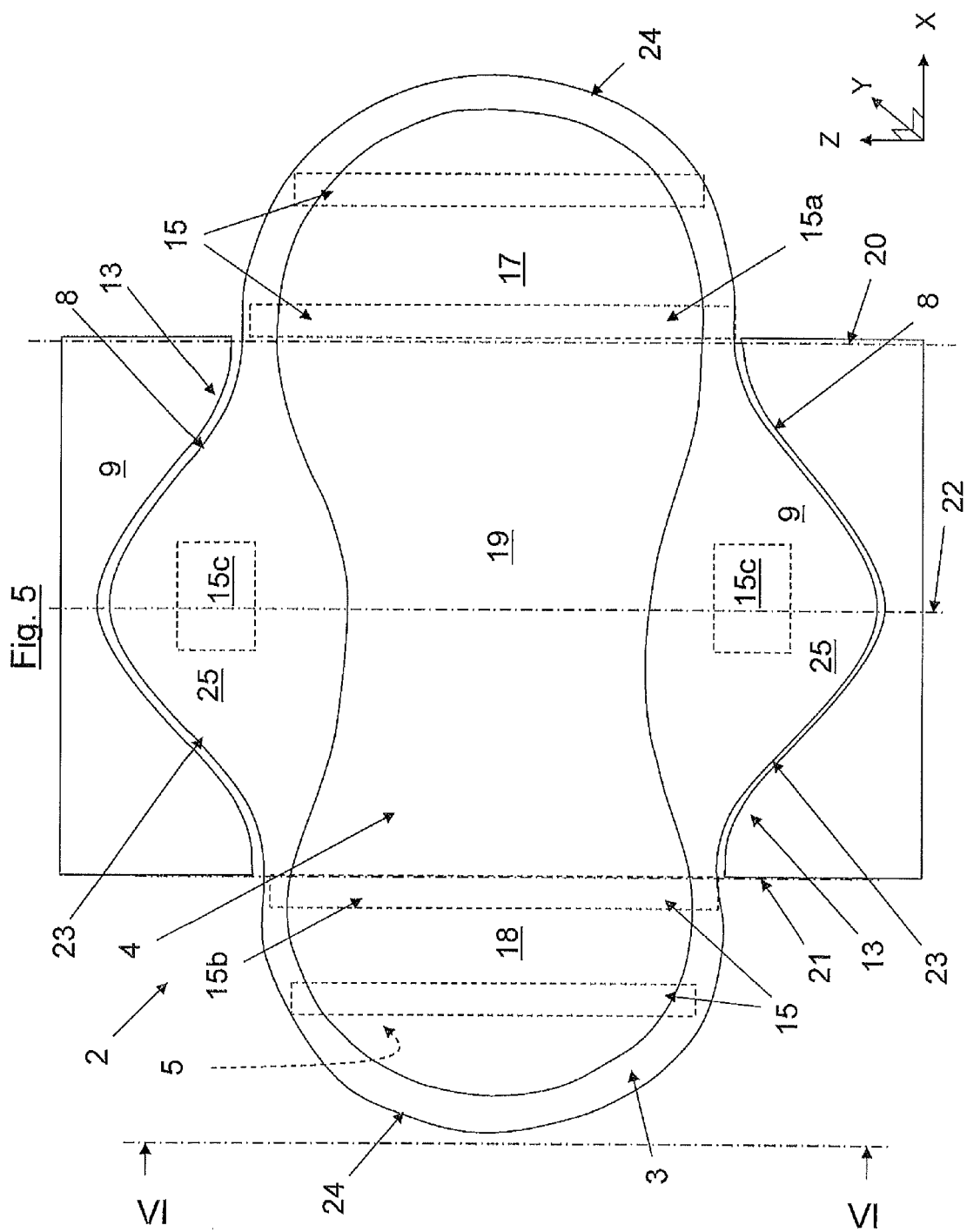
FIG. 5 schematically shows a third example of the packet in FIG. 2, in an unfolded position.

FIG. 5 schematically shows a third example of the packet 1 in FIG. 2, in an unfolded position. FIG. 5 differs from FIG. 3 only in that the longitudinally extending edges 23, hence also the first tearing lines 8, are curved so that a part of the backsheet 3 in the central portion 19 has an extension away from the absorbent body 4, i.e. in the lateral direction Y, forming so called wings or flaps 25. Here, "flaps" are defined as means for attachment against an undergarment. Preferably, the flaps 25 are arranged to be folded about side edges in the groin area of the undergarment, for attachment against an outside of the undergarment. The absorbent article 2 is arranged to be positioned on an inside of the undergarment and the fastening means 15 are arranged to be attached to the inside of the undergarment. In FIG. 5, the backsheet 3 has a different contour than the absorbent body 4, but the absorbent body 4 may have the same shape. In FIG. 5 the contour of the absorbent body 4 is in the form of an hour-glass, but other shapes are possible according to what has been described in connection to FIG. 3. The flaps 25 are formed when the first tear tabs 9 are removed from the packet 1, i.e. when a user grabs the first tear tabs 9 and pulls the first tear tabs 9 away from the remaining portion of the packet 1, i.e. the absorbent article 2, by rupturing the backsheet 3 material along the first tearing lines 8.

FIG. 5 shows that each flap 25 comprises a third fastening means 15c arranged to be attached to the outside of the undergarment when the flaps have been folded about the side edges of the under garment. The third fastening means 15c may have any suitable shape.

Figure 6:
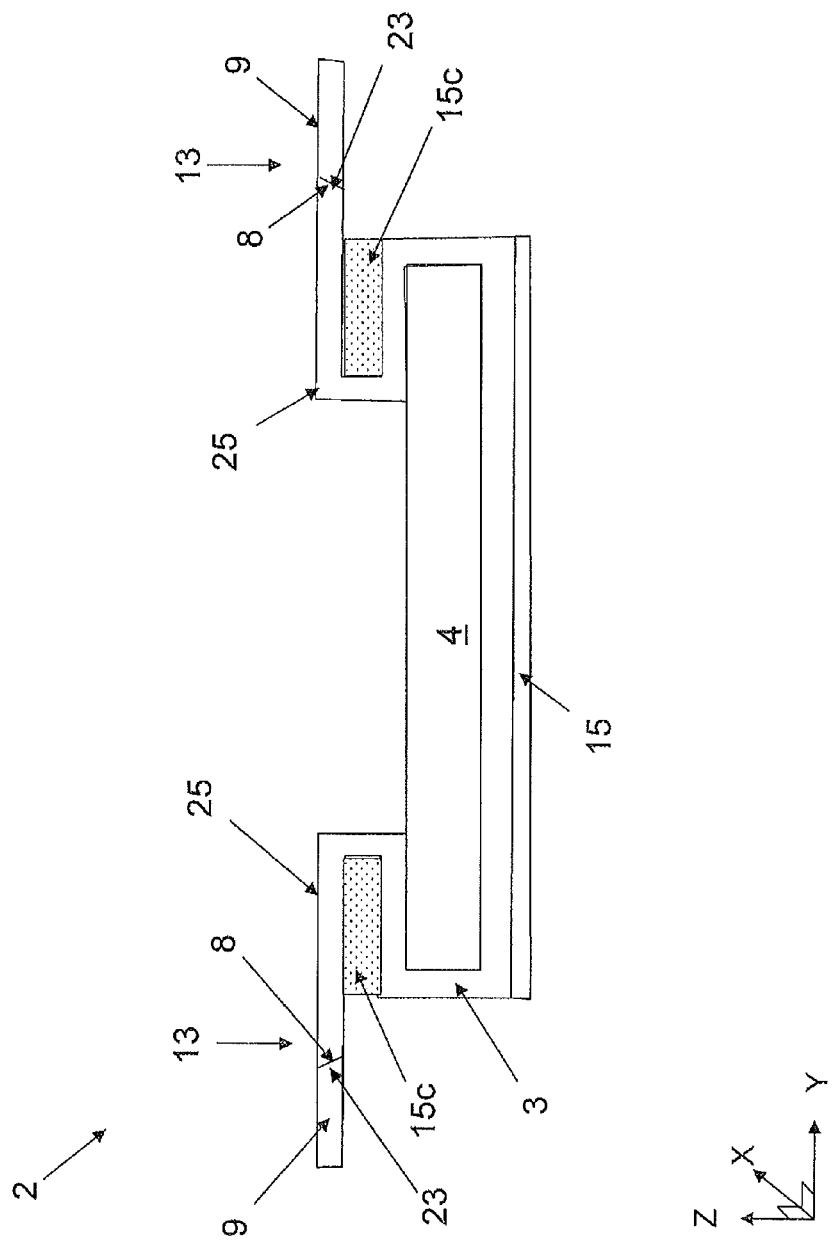
FIG. 6 schematically shows a side view of FIG. 5 along line VI-VI, with folded flaps.

FIG. 6 schematically shows a side view of FIG. 5 along line VI-VI, with folded flaps 25. FIG. 6 shows the absorbent article 2 viewed from the rear portion 18 with the flaps 25 being folded over the absorbent body 4. In FIG. 6 each flap 25 has been double folded, i.e. folded over itself, so that the third fastening means 15c have been concealed in the pleat formed by the double folding. One advantage of double folding the flaps 25 is that the third fastening means 15c will not adhere to any other part of the absorbent article 2 when the absorbent article 2 is folded and formed into the packet 1. Furthermore, since the first tear tabs 9 are positioned mainly in the central portion 19, in order to create the flaps 25 and to seal the packet 1, the double folding of the flaps also allows for the first tear tabs 9 to extend in the lateral direction so that the packet 1 can be sealed by the first sealing means 10 according to FIG. 1.

One alternative to the embodiment shown in FIG. 6 is to keep the flaps 25 unfolded and to apply a removable cover strip for the third fastening means 15c. The cover strips are necessary since the third fastening means 15c would not be concealed in this embodiment, but would be positioned on the outside of the packet 1 along with the first tear tabs 9.

Figure 7:
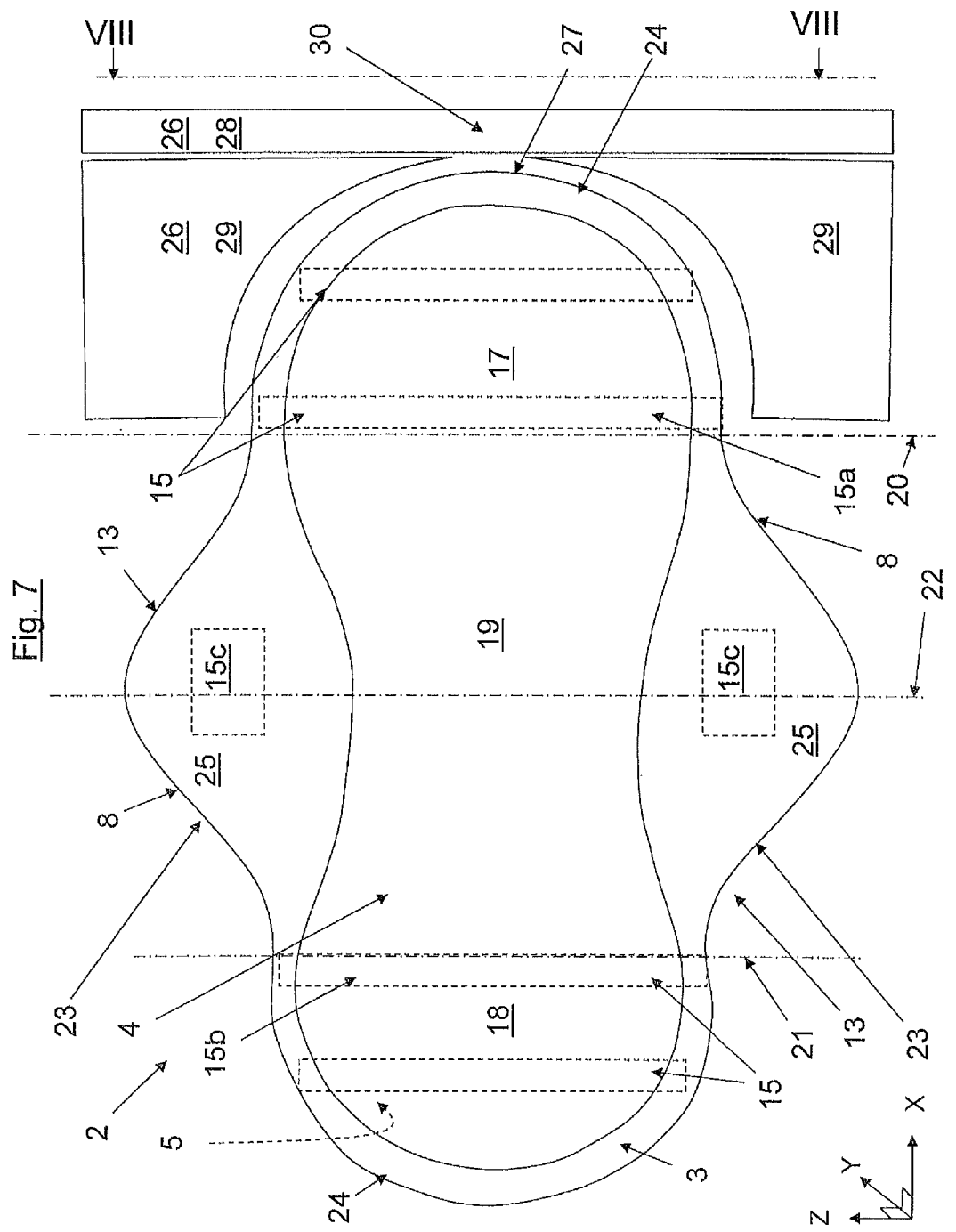
FIG. 7 schematically shows an example of the packet in FIG. 1, in an unfolded position.

FIG. 7 schematically shows an example of the packet 1 in FIG. 1, in an unfolded position. FIG. 7 differs from FIG. 5 in that second tear tabs 26 are positioned in the front portion 17 of the absorbent article 2. Hence, the flaps 25 are not formed when the first tear tabs 9 are removed, but the flaps 25 are pre-formed in the backsheet 3 material. However, the front portion 17 is formed when the second tear tabs 26 are removed from the packet, i.e. when a user grabs the second tear tabs and pulls the second tear tabs away from the remaining portion of the packet 1, i.e. the absorbent article 2, by rupturing the backsheet 3 material along second tearing lines 27.

FIG. 7 shows that the second tear tabs 26 are formed in an essentially triangular shape and that the second tearing lines 27 meet in a transition area between the second tear tabs 26 and that each second tear tab 26 ends where the second tearing lines 27 meet. This arrangement gives two second tear tabs 26 that are to be removed when the packet 1 shall be opened. However, the second tear tabs 26 may be arranged in one piece with the second tearing line 27 following the contour of the laterally extending edge 24 that is to be created upon removal of the second tear tab 26. The second tear tab 26 then has an extension in the longitudinal direction such that the backsheet 3 material has an essentially rectangular part 28 (shown with a broken line) in addition to the two triangular parts 29 shown in FIG. 7. The rectangular part 28 can be used as sealing means for a third sealed portion 30 of the packet 1 and may be folded over the folded parts. The second tear tab 26 may have any suitable shape and is not restricted to two triangular parts and a rectangular part. It depends on the shape of the front portion 17 and how the second tear tab 26 is going to be used. Hence, the second tear tab 26 may be one or several rectangular pieces, one or several triangular pieces, or one or several pieces with another suitable geometry. Furthermore, the second tear tab 26 may be positioned at the rear portion instead of the front portion.

Furthermore, in order to seal a packet formed from the absorbent article in FIG. 7, the absorbent article cannot be folded in the same manner as described in connection to FIG. 2, but reference is made to FIGS. 12, 13, 14 and 22. The absorbent article 2 must be folded or rolled from one end of the absorbent article 2, namely that end of the absorbent article that does not comprise the second tear tabs 26. In FIG. 7 the rear portion 18 should be folded or rolled over the central portion 19 and then over the front portion 17. The parts of the second tear tabs 26 that extend in the lateral direction can then be used for sealing the packet 1 and additional tearing lines may be applied accordingly.

Figure 8:
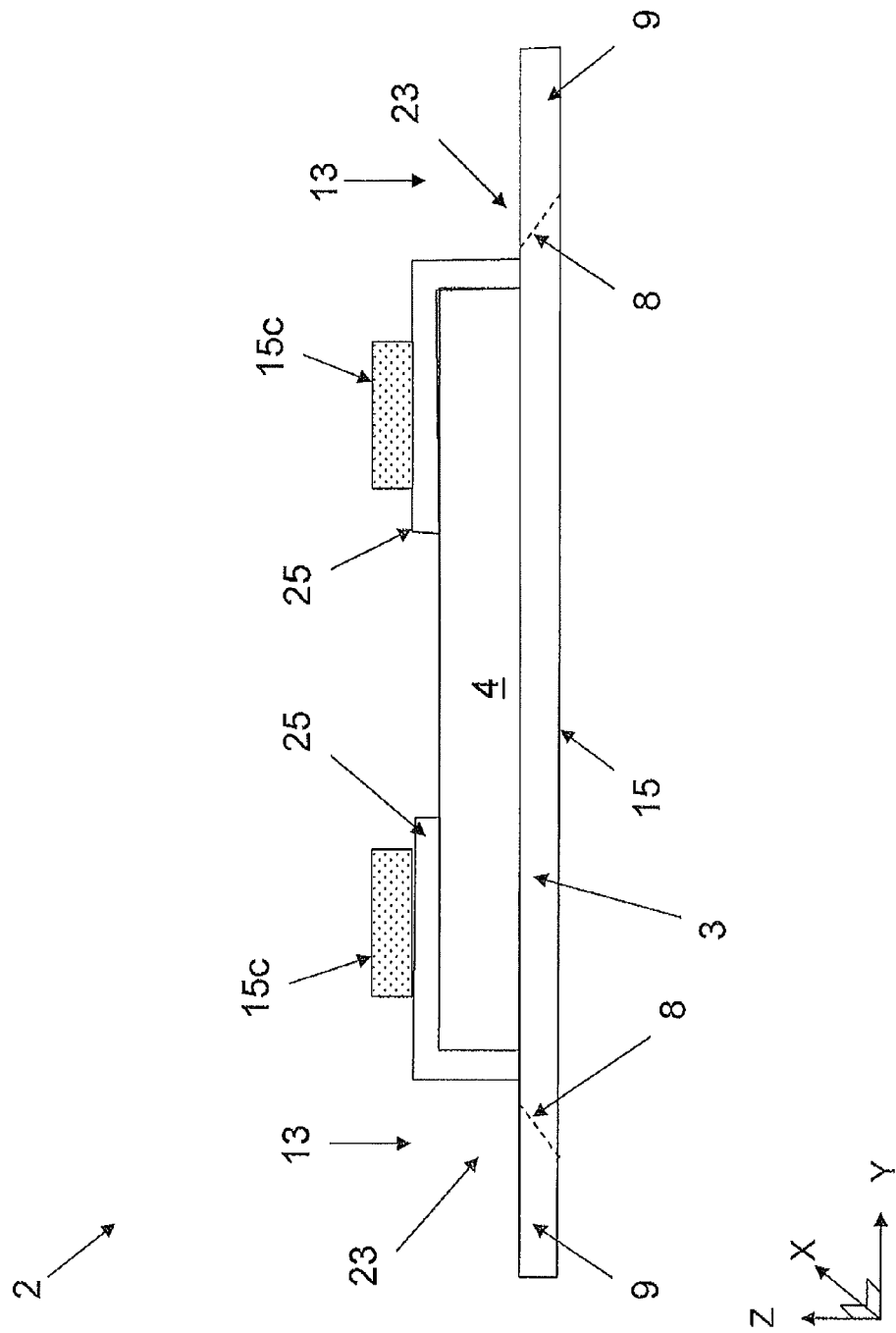
FIG. 8 schematically shows a side view of FIG. 7 along line VIII-VIII, with folded flaps.

FIG. 8 schematically shows a side view of FIG. 7 along line VIII-VIII, with folded flaps 25. FIG. 6 shows the absorbent article 2 viewed from the front portion with the flaps 25 being folded over the absorbent body. Since the first tear tabs 9 are positioned mainly in the central portion 19, and in order to create the flaps 25 and to seal the packet 1, the folding of the flaps 25 also allows for the first tear tabs 9 to extend in the lateral direction so that the packet 1 can be sealed by the first sealing means 10 in the first sealed portions 14 according to FIG. 1.

In FIG. 8 the flaps 25 are folded over the absorbent body 4 and the third fastening means 15c faces away from the absorbent body. There is no need for a cover strip when the absorbent article is rolled or folded according to FIG. 12 so that the backsheet of the rolled/folded part lies against the third fastening means as a cover.

Figure 9:
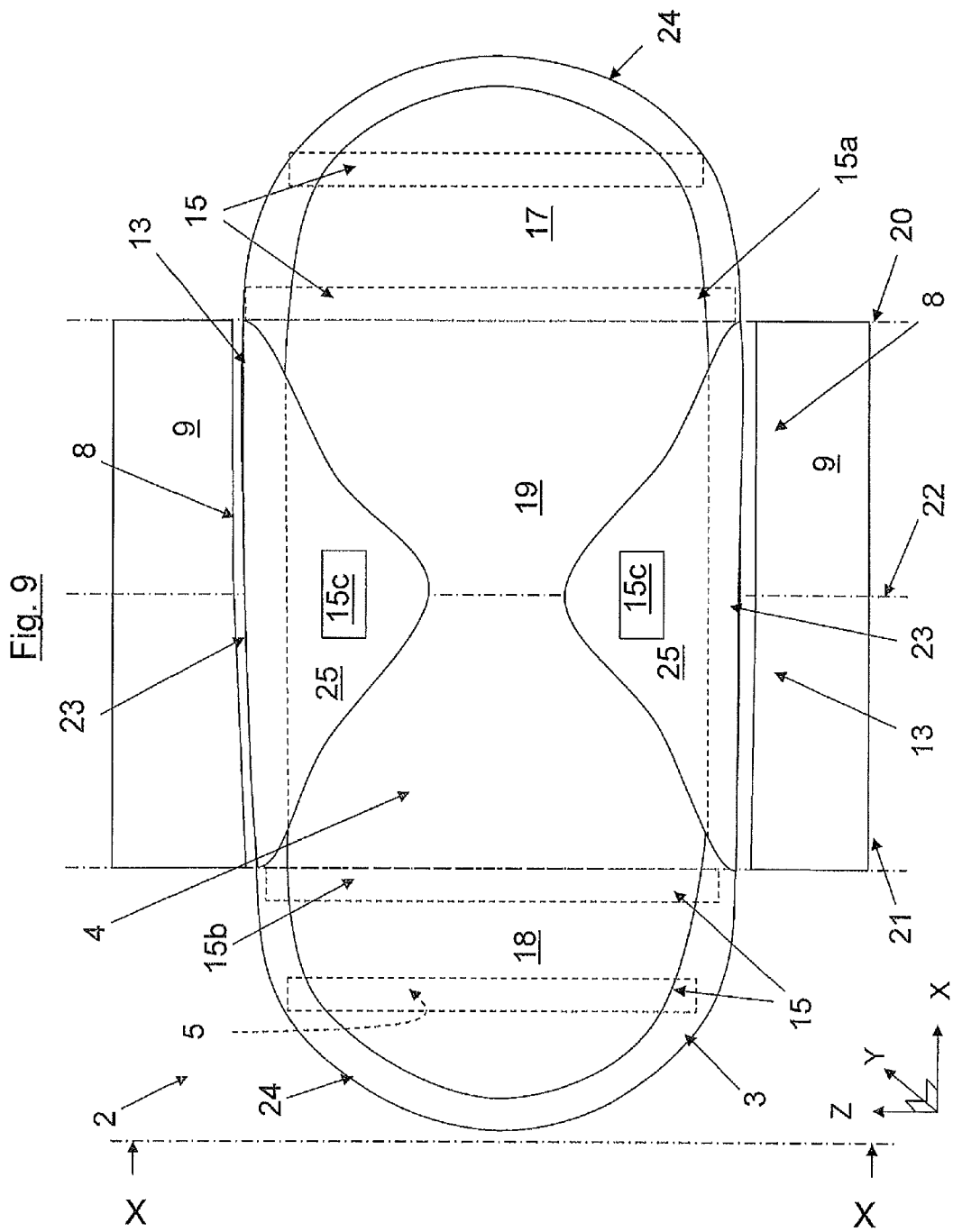
FIG. 9 schematically shows a fourth example of the packet in FIG. 2, in an unfolded position.

FIG. 9 schematically shows a fourth example of the packet 1 in FIG. 2, in an unfolded position. FIG. 9 comprises all features discussed in connection to FIG. 5, but the flaps 25 are not part of the backsheet 3. The flaps 25 are separate pieces of material that have been attached to the absorbent article 2. The attachment can be done by welding, mechanical machining, use of an adhesive, or any other suitable means for attachment. The flaps 25 may be attached to the backsheet 3 or the absorbent body 4.

In FIG. 9, the flaps 25 are folded over the absorbent body 4 and the third fastening means 15c are arranged on the flaps 25 on that side of the flaps 25 that faces away from the absorbent body when being folded as in FIG. 9.

FIG. 9 shows that the first tear tabs 9 are positioned in the central portion 19 of the absorbent article and that the first tear tabs 9 extend in the lateral direction and in the longitudinal direction. The first tearing lines 8 follow the contour of the absorbent article 2, i.e. the contour of the longitudinally extending edges 23. The first tearing lines 8 do not follow the contour of the flaps 25.

Figure 10:
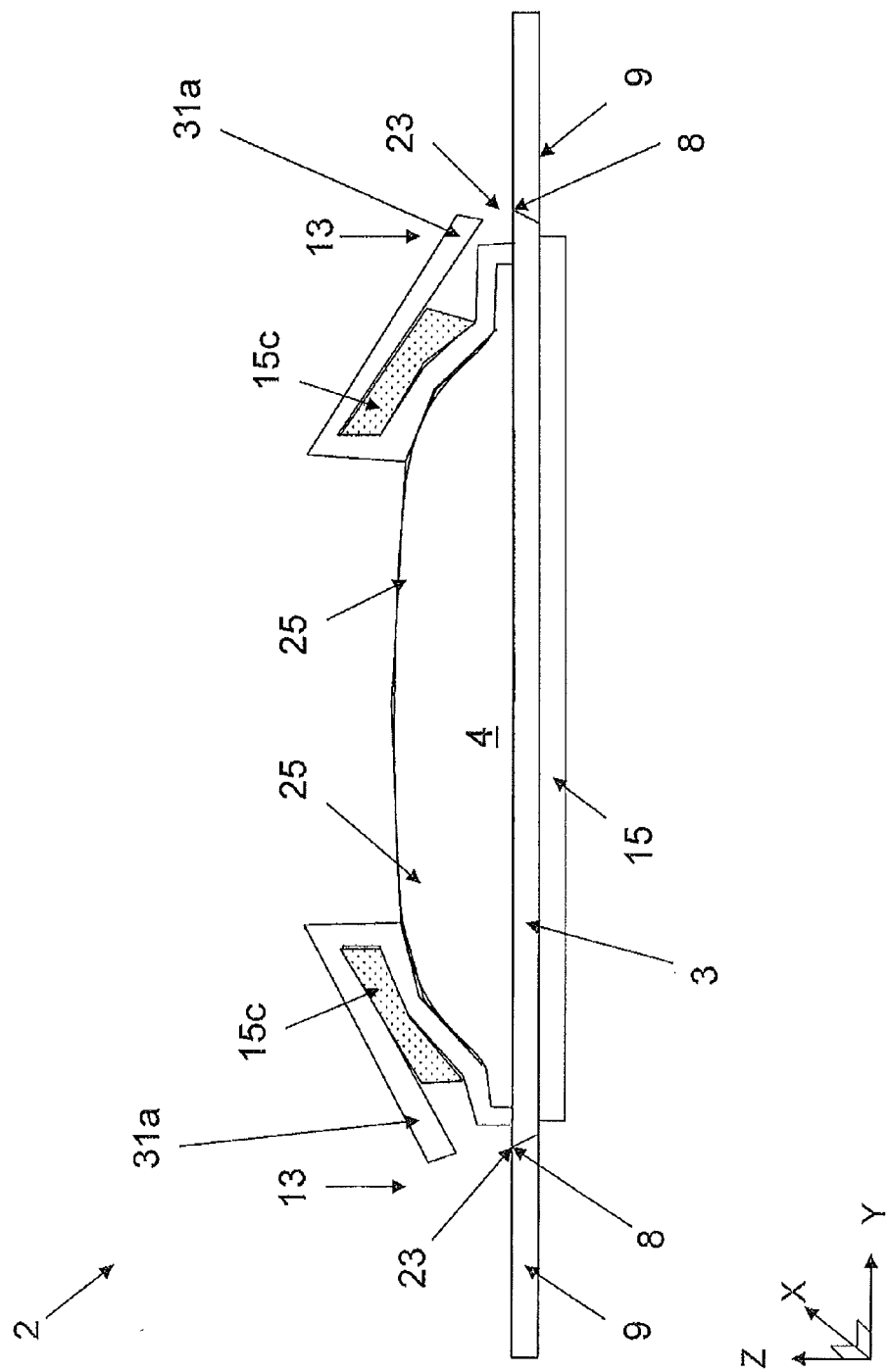
FIG. 10 schematically shows a side view of FIG. 9 along line X-X, with folded flaps according to one embodiment.

FIG. 10 schematically shows a side view of FIG. 9 along line X-X, with folded flaps 25 according to one embodiment. FIG. 10 shows the absorbent article 2 viewed from the rear portion 18 with the flaps being folded over the absorbent body 4. With reference to FIG. 6, FIG. 10 shows that each flap 25 has been double folded, i.e. folded over itself, so that the third fastening means 15c have been concealed in the pleat formed by the double folding. One advantage of double folding the flaps 25 is that the third fastening means 15c will not adhere to any other part of the absorbent article 2 when the absorbent article 2 is folded and formed into the packet. The flaps 25 may comprise a gripping means 31a which is free from the third fastening means 15c so that a user can grip the flap 25 and unfold it before use. When the flaps 25 are unfolded, the third fastening means 15c are revealed and can be used for fastening the flaps 25 to an outside of an undergarment.

Figure 11:
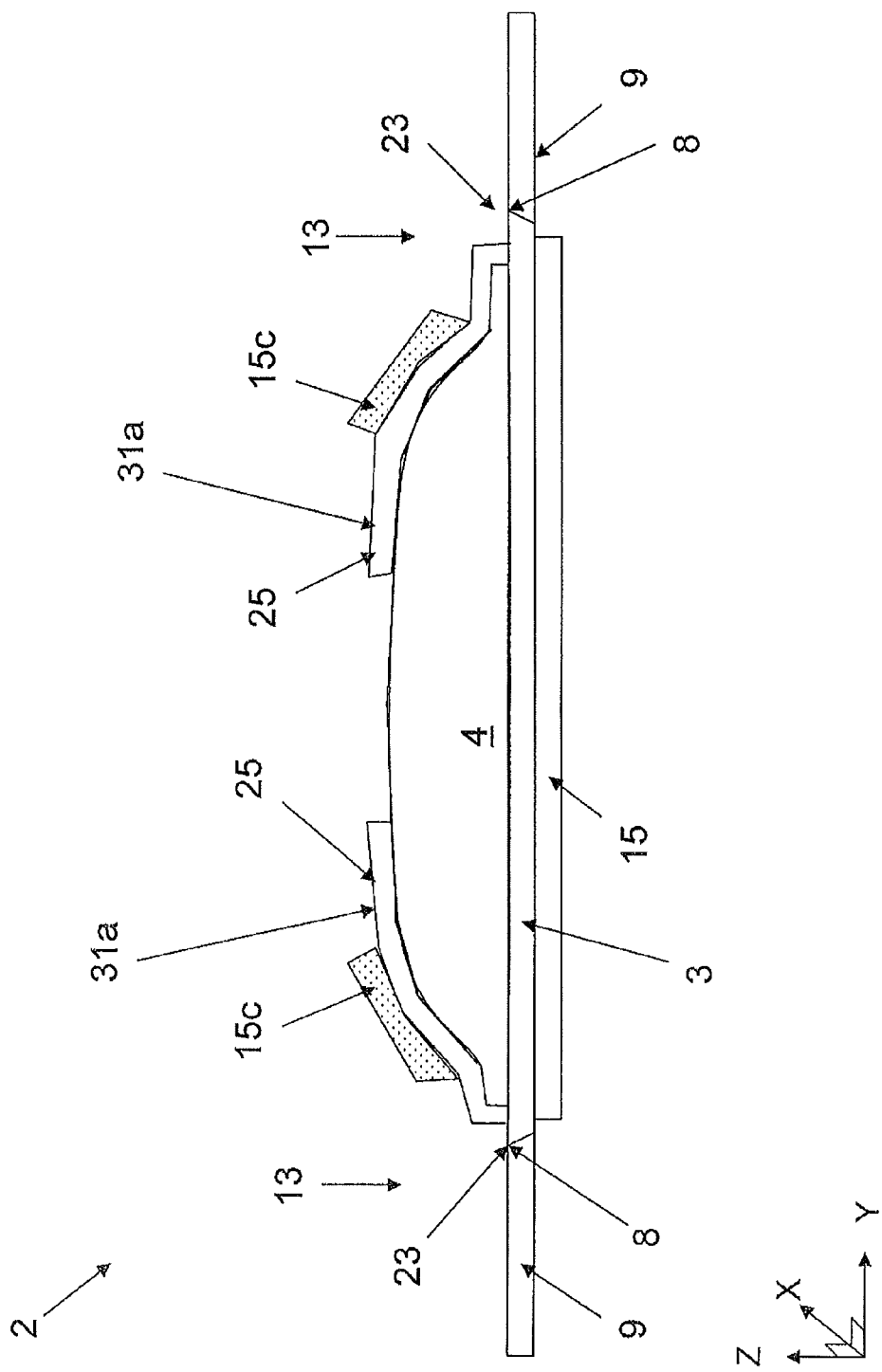
FIG. 11 schematically shows a side view of FIG. 9 along line X-X, with folded flaps according to another embodiment.

FIG. 11 schematically shows a side view of FIG. 9 along line X-X, with folded flaps 25 according to another embodiment than FIG. 10. FIG. 11 shows that the flaps 25 are folded over the absorbent body 4, but that the flaps 25 are not folded over themselves. In this position, the third fastening means 15c faces away from the absorbent article 2 and must either be covered with a removable cover strip (not shown), if the absorbent article 2 is folded as shown in FIG. 2, or may be covered by the backsheet 3 if the absorbent article is folded or rolled according to FIGS. 12, 13, 14 and 22.

Figure 12:
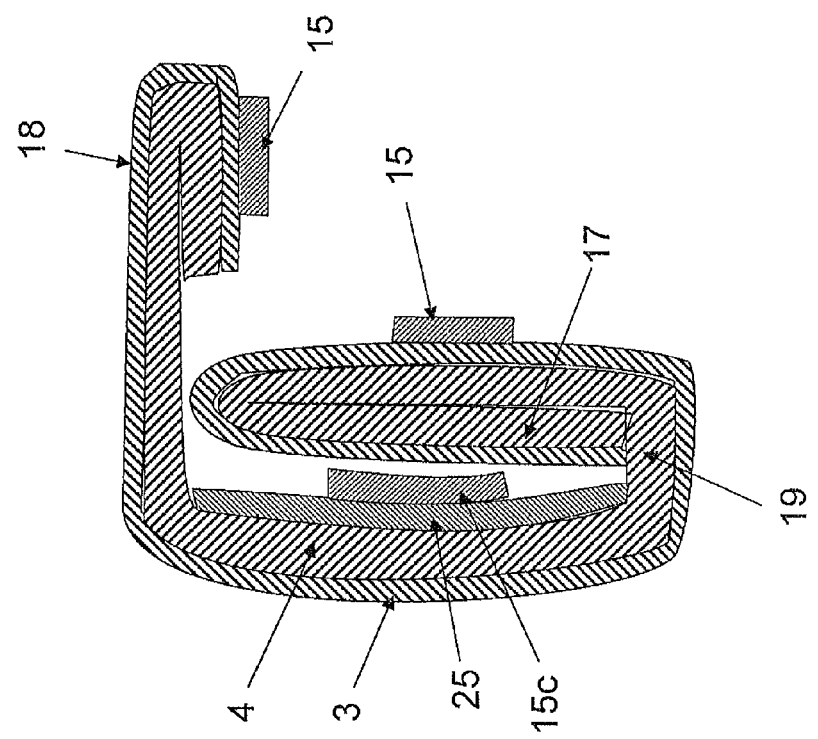
FIG. 12 schematically shows a cross-section along a line A-A in FIG. 1 according to a second embodiment of the invention.

FIG. 12 schematically shows a cross-section along a line A-A in FIG. 1 according to a second embodiment of the invention. FIG. 12 shows that the absorbent article 2 is folded or rolled from one end of the absorbent article, namely that end of the absorbent article that does not comprise any first or second tear tabs 26. FIG. 12 shows the packet semi-closed, i.e. with a last portion being unfolded. In FIG. 12 the rear portion 18 is folded over itself and the front portion 17 is rolled over the central portion 19 and is then intended to be folded or rolled over the corresponding double folded rear portion 18. The invention is not limited to this embodiment, but the front portion 17 may folded over itself and the rear portion 18 may be rolled over the central portion 19 and then folded or rolled over the corresponding double folded front portion 17.

Second tear tabs can be arranged in the front portion or the rear portion, dependent on which part of the absorbent article 2 that is folded or rolled towards the absorbent body in the central portion. If the front portion is folded or rolled, the rear portion comprises the tear tabs. However, first tear tabs 9 may be positioned along the entire longitudinally extending edges, and may also extend along at least a part of the laterally extending edge. The parts of the first and/or second tear tabs 9, 26 that extend in the lateral direction can then be used for sealing the packet and first and/or second tearing lines 8, 27 may be applied accordingly.

FIG. 12 shows that the end of the absorbent article 2 that is not rolled is folded over itself once so that the outside 5 of the backsheet of the once folded part faces the outside of the backsheet of the folded or rolled part of the absorbent article 2.

In FIG. 12, the absorbent article 2 is folded in such a way that the rear portion is double folded in such a way the absorbent body 4 faces itself and in such a way that the front portion 17 is rolled in a direction towards the central portion 19, and in such a way that at least a part of the outside of the backsheet 3 in the front portion 17 is interconnected via the fastening means 15 to at least a part of the outside of the backsheet 3 in the rear portion 18.

Figure 13:
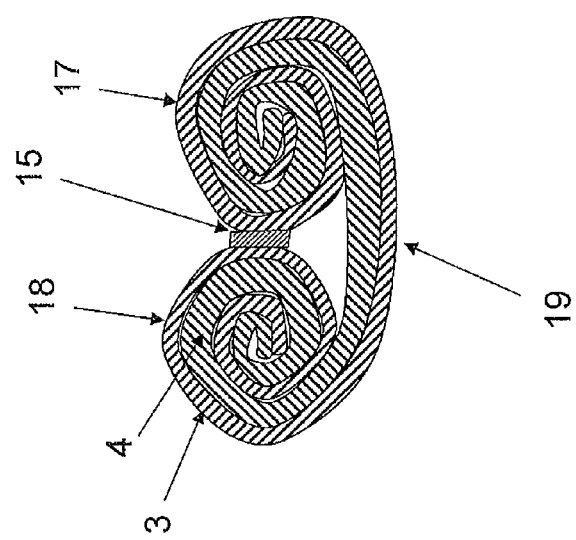
FIG. 13 schematically shows a packet for an absorbent article according to a third embodiment of the invention.

FIG. 13 schematically shows a packet 1 for an absorbent article according to a third embodiment of the invention. In FIG. 13, the absorbent article 2 has been rolled in a direction from the front portion 17 towards the central portion 19 and from the rear portion 18 to the central portion 19 in such a way that at least a part of the outside 5 of the backsheet of the front portion 17 is interconnected via the fastening means 15 to at least a part of the outside 5 of the backsheet 3 of the rear portion 18.

The first tearing lines 8 and the first tear tabs 9 are arranged in the backsheet 3 in the same manner as been described above in connection to any one of FIGS. 1-12, i.e. along the longitudinally extending side edges 12a of the packet 1. The first tear tabs 9 may extend in the lateral direction in such way that the first tear tabs 9 comprises a sealing portion that can be folded over the longitudinally extending side portions 11a of the packet 1 for sealing the longitudinally extending side portions 11a. The first tear tabs 9 may also comprise a gripping means for facilitating the opening of the packet by the user being able to grab the gripping means for pulling. FIGS.

19 and 21 show that the above described sealing of the longitudinally extending side portions 11a.

Figure 14:
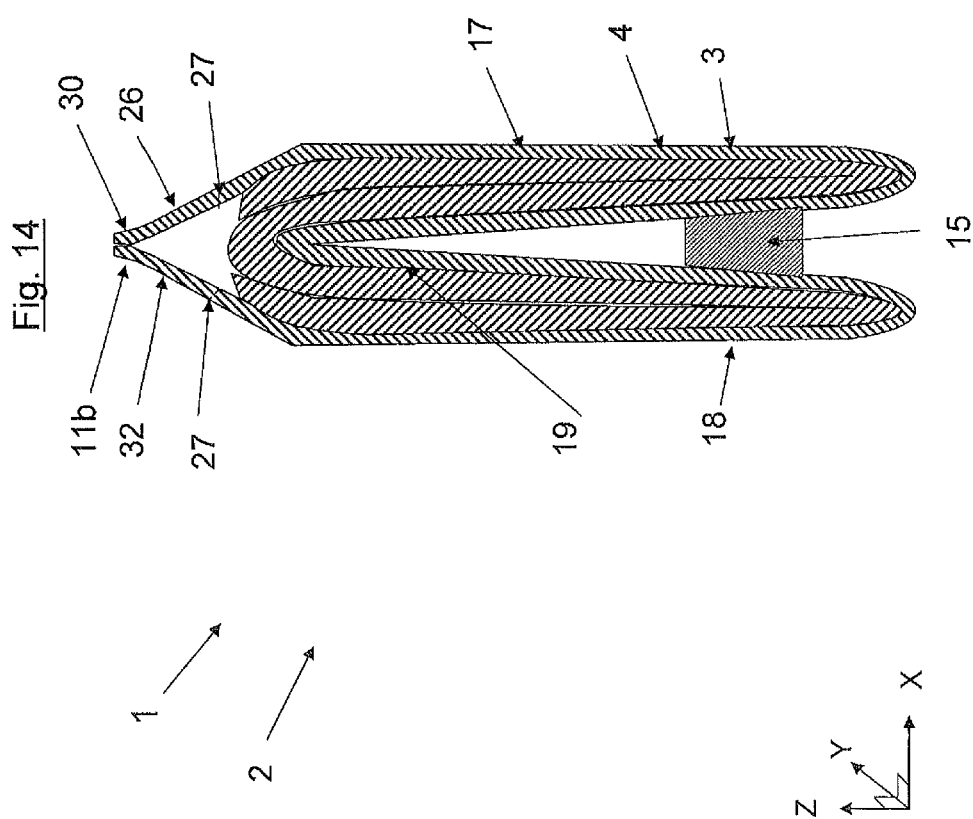
FIG. 14 schematically shows a cross-section along a line B-B in FIG. 13 according to a fourth embodiment of the invention.

FIG. 14 schematically shows a cross-section of a packet 1 according to a fourth embodiment of the invention. The absorbent article 2 comprises, in its unfolded position, the longitudinal direction and the lateral direction perpendicular to the longitudinal direction and a thickness direction perpendicular to the plane described by the longitudinal direction and the lateral direction. The absorbent article 2 comprises, in the longitudinal direction, the front portion 17, the rear portion 18 and the central portion 19 therebetween. The absorbent article 2 is folded in such a way that the absorbent body 4 in the front portion 17 faces a part of the absorbent body 4 in the central portion 19 and in such a way that the absorbent body 4 in the rear portion 18 faces a part of the absorbent body 4 in the central portion 19, and in such a way that at least a part of the outside 5 of the backsheet in the central portion 19 is interconnected via the fastening means 15 to at least a part of the outside 5 of the backsheet 3 in another part of the central portion 19. Hence, the absorbent article 2 is folded in a zig-zag pattern allowing the fastening means 15 to be hidden in the packet in such a way that only the backsheet 3 is in contact with the fastening means 15.

FIG. 14 shows that the backsheet 3 comprises second tear tabs 26 in the form of two laterally extending edge portions 32 being folded over each other forming a third sealed portion 30 for sealing the laterally extending side portion 11b of the packet 1. The third sealed portion 30 comprises second tearing lines 27 for separation of the second tear tabs 26 from the backsheet 3 from the packet 1 when the absorbent article 2 is in its folded position, or wherein the third sealed portion 30 is separable or openable, for opening the packet 1. The third sealed portion 30 is arranged for sealing the gap between the absorbent body 4 in the rear portion 18 and the absorbent body 4 in the front portion 17.

Figure 15:
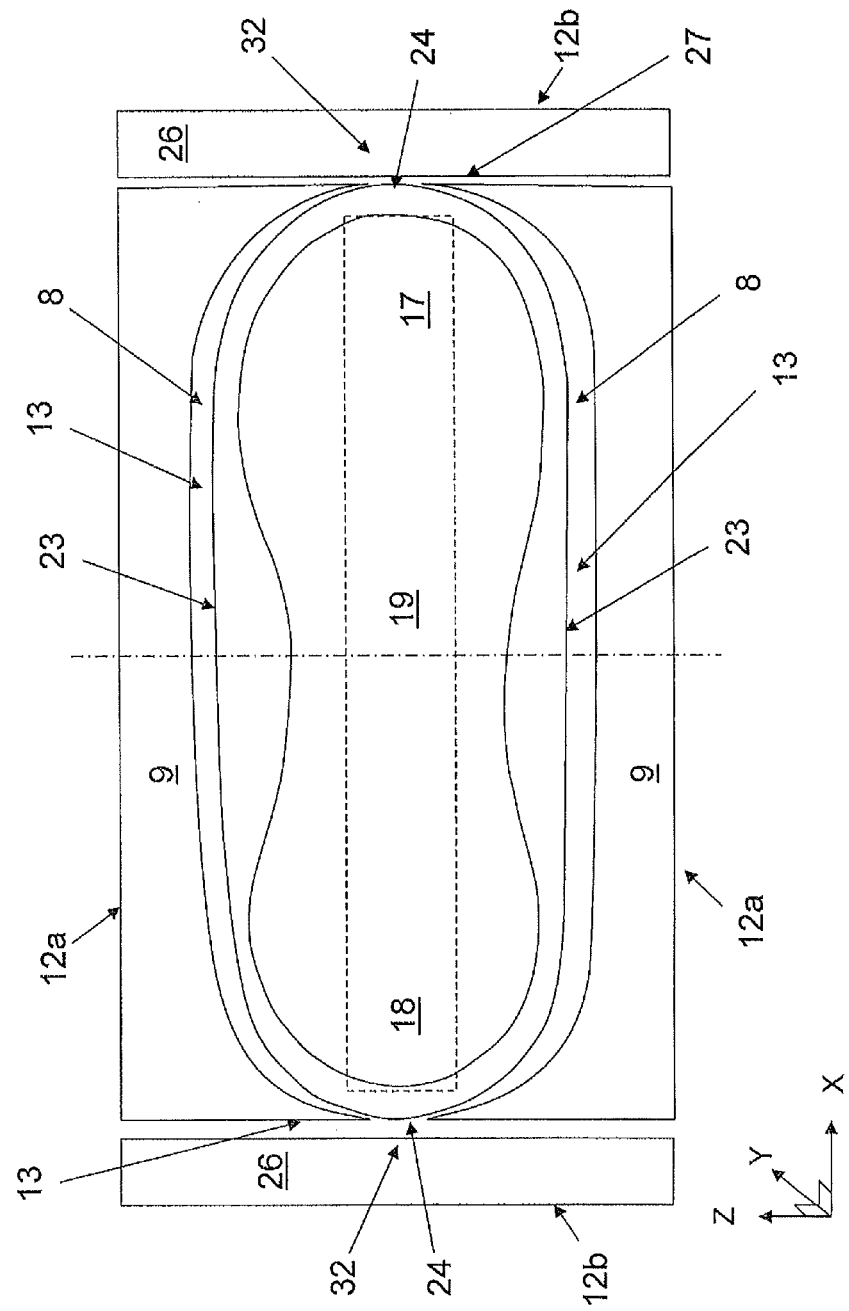
FIG. 15 schematically shows a first example of the packet in FIG. 14, in an unfolded position.

FIG. 15 schematically shows a first example of the packet 1 in FIG. 14, in an unfolded position. FIG. 15 shows that the first tear tabs 9 are arranged along the longitudinally extending side edges 12a of the packet 1, i.e. in the longitudinally extending edge portions 13 of the backsheet 3, and that the second tear tabs 26 are arranged along the laterally extending side edge 12b of the packet, i.e. in the laterally extending edge portion 32 of the of the rear portion 18 and the front portion 17. The first tearing lines 8 are arranged along the longitudinally extending side edges 12a of the packet 1, i.e. in the longitudinally extending edge portions 13, and the second tearing lines 27 are arranged along the laterally extending side edge 12b of the packet 1, i.e. in the laterally extending edge portion 32 of the front portion 17 and the laterally extending edge portion 32 of the rear portion 18 of the backsheet 3 respectively. The first and second tearing lines 27 are arranged to form the backsheet 3, and hence the absorbent article 2, when the first and second tear tabs 26 are removed from the packet 1 thus creating the longitudinally extending edges 23 and the laterally extending edges 24 of the absorbent article 2.

Figure 16:
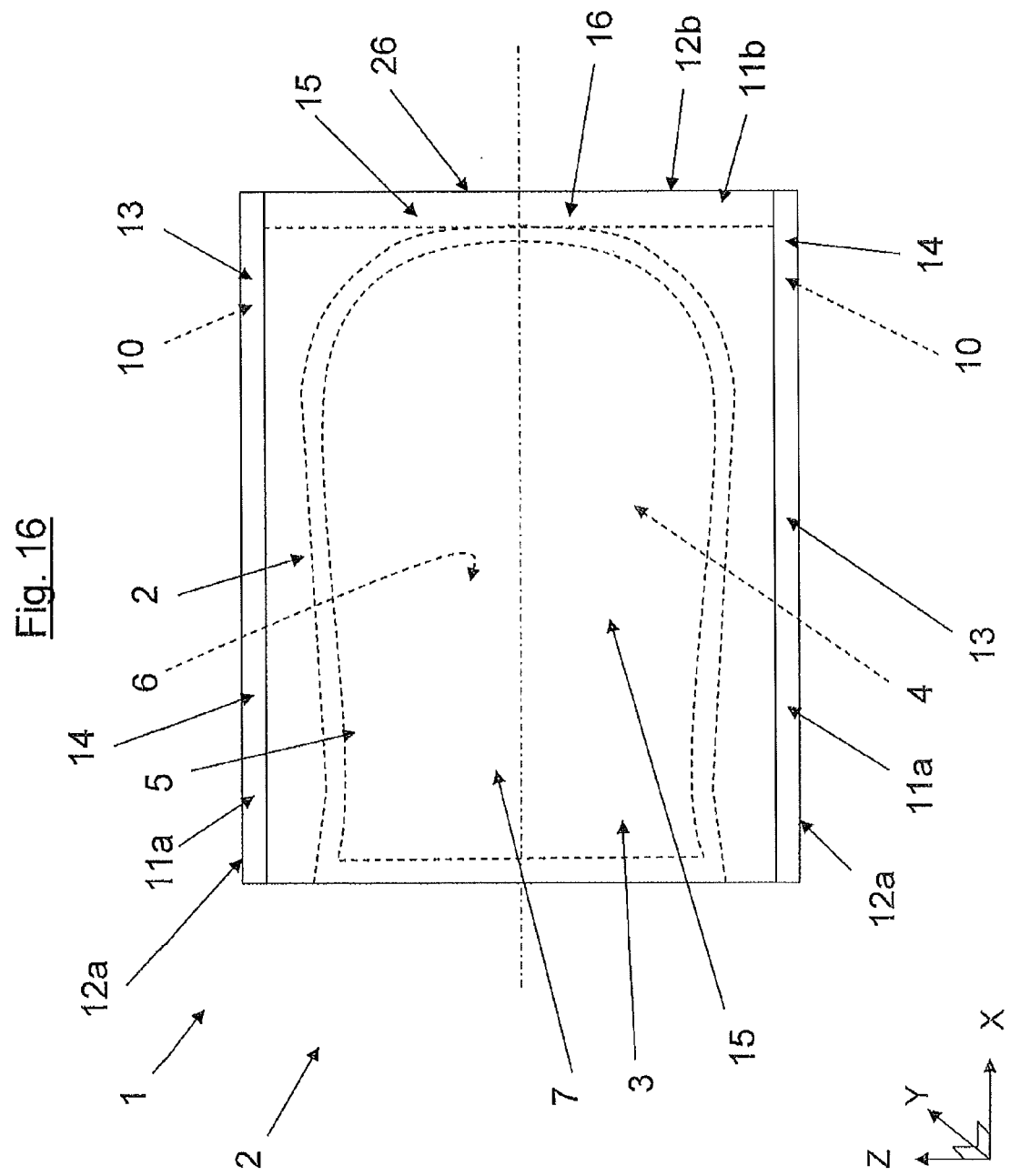
FIG. 16 schematically shows a packet for an absorbent article according to the invention.

FIG. 16 schematically shows a packet for an absorbent article 2 according to the invention. FIG. 16 shows that the first sealing means 10 in the first sealed portion 14 is of a kind that can be separated or opened without removing any material from the backsheet 3. Hence, here the first sealed portion 14 is defined by sections of the backsheet 3 that are bonded together by the first sealing means 10 and that can be opened by breaking the bond within the first sealing means 10 or the bond between one attachment surface of the first sealing means 10 and the corresponding part of the outside 5 of the backsheet 3. As been discussed before, the fastening means 15 may be positioned on the backsheet 3 and will be hidden within the packet 1 according to the invention. FIG. 16 shows that the fastening means 15 are arranged on the backsheet 3 in such a way that when the absorbent article is folded into the packet, the fastening means 15 becomes positioned along the laterally extending side edge 12b of the packet 1. The fastening means 15 may form a seal in the laterally extending openable second sealed portion 16, but the second sealed portion may also or instead comprise the removable second tear tabs 26. In the latter case, the fastening means 15 may be positioned anywhere on the backsheet 3, as long as the fastening means 15 are hidden within the packet 1.

Figure 17:
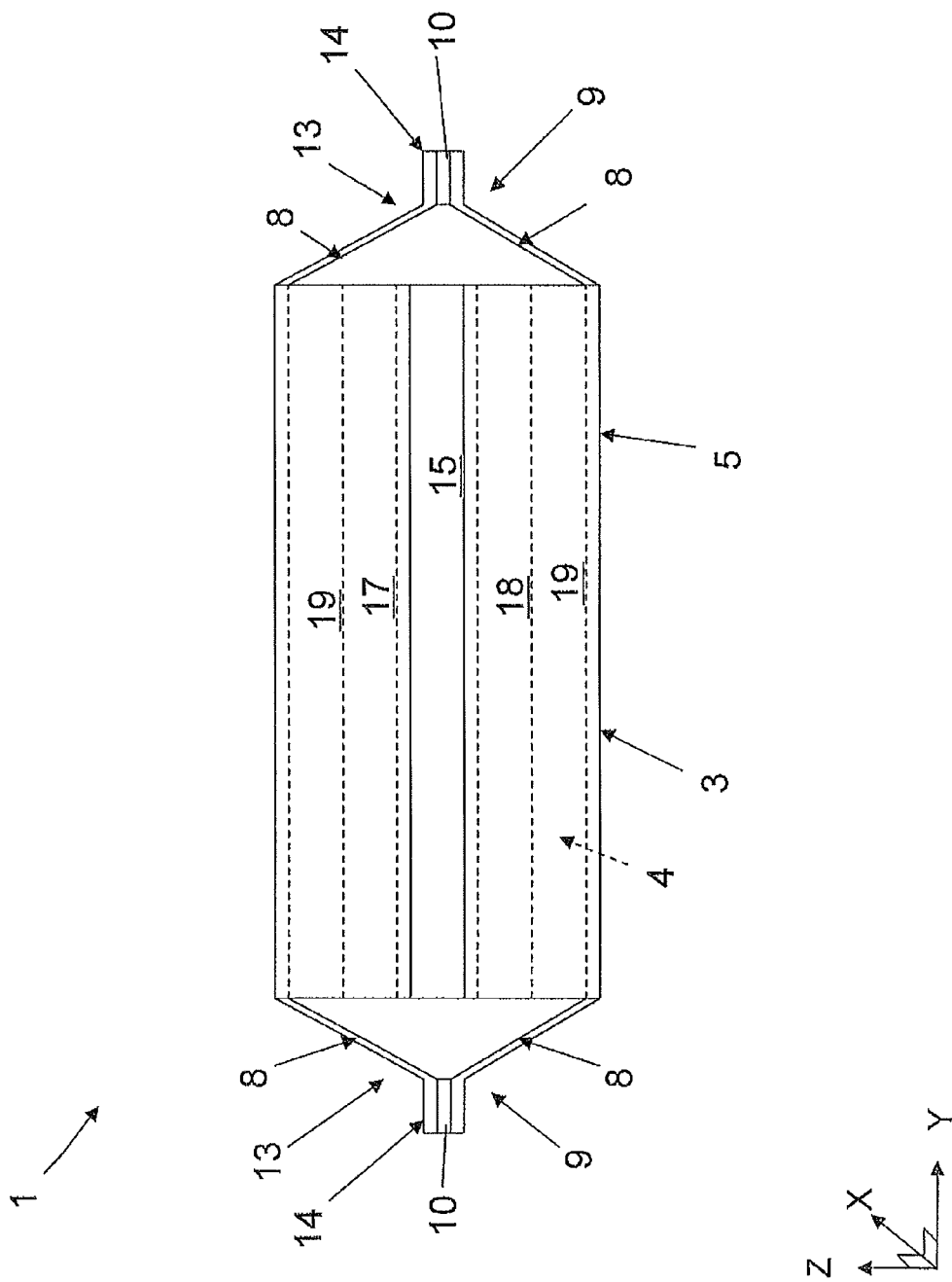
FIG. 17 schematically shows a front view of a packet 1 according to the invention.

FIG. 17 schematically shows a front view of a packet 1 according to the invention. FIG. 17 shows that the first tear tabs 9 are positioned in the central portion 19 and that no other tear tabs are present in the packet 1. FIG. 17 shows that the first sealing means 10 are positioned in the first sealed portions 14 between the longitudinally extending edge portions 13 of the backsheet 3 that form the first tear tabs 9. FIG. 17 shows that the first tearing lines 8 are positioned at a distance from the first sealed portions 14, between the first sealed portions 14 and the absorbent body 4. Hence, upon removal of the first tear tabs 9 the absorbent article becomes shaped in the central portion 19 accordingly. Reference is made to FIGS. 1-6 and 9-11.

Figure 18:
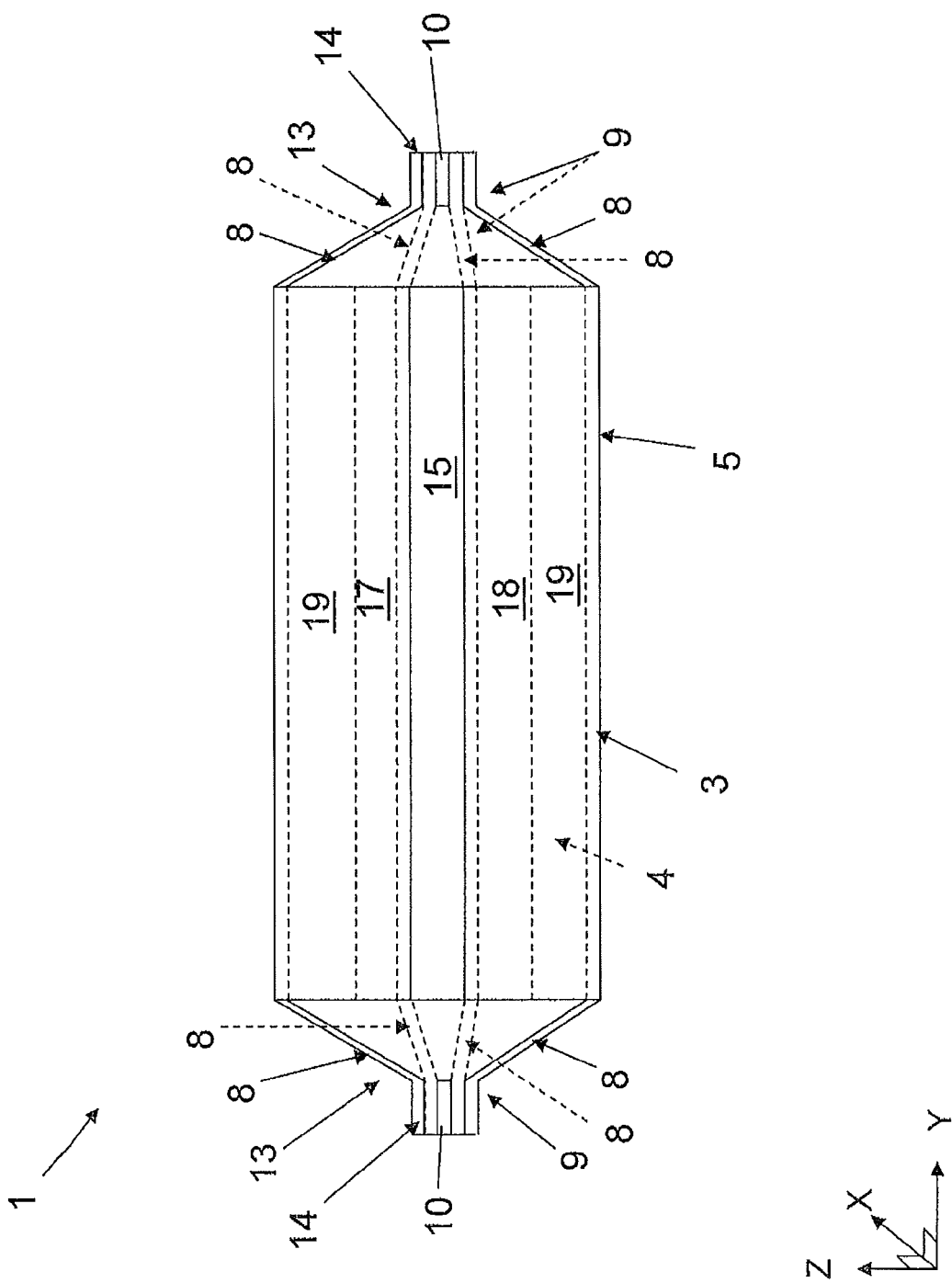
FIG. 18 schematically shows a front view of a packet 1 according to the invention.

FIG. 18 schematically shows a front view of a packet 1 according to the invention. FIG. 18 shows that the first tear tabs 9 are positioned in the central portion 19 and the front portion and the rear portion 18. This solution can be used on the double folded or rolled absorbent article shown in any one of FIGS. 1-16.

Figure 19:
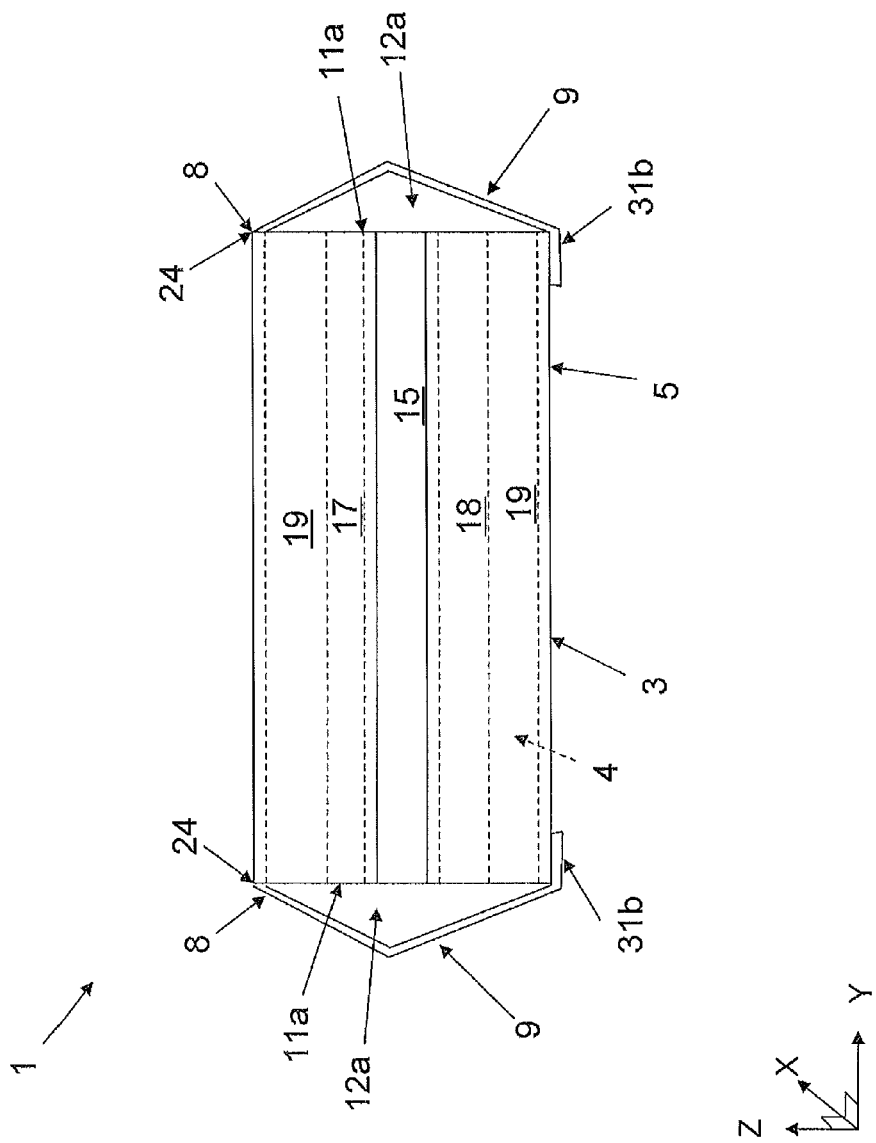
FIG. 19 schematically shows a front view of a packet according to the invention.

FIG. 19 schematically shows a front view of a packet according to the invention. FIG. 19 shows that the first tear tabs 9 are positioned in half the central portion, either towards the front portion or the rear portion. FIG. 19 shows that the first tear tabs 9 can be folded over the longitudinally extending side edges 12a of the packet 1 and attached to the outside of the backsheet 3. This solution can be used on the double folded or rolled absorbent article shown in any one of FIGS. 1-13. With regard to FIG. 13, the first tear tabs 9 may be positioned in a part of the central portion 19 in such a way that, after the rolling into the packet 1, the first tear tabs 9 can be folded to cover the rolled portions of the longitudinally extending side portions 11a. Hence, if the front portion 17 is rolled in the same extent as the front portion 17 the first tear tabs 9 may be positioned in a central part of the central portion 19.

The first tear tabs 9 can be removed by gripping a gripping means 31b for unfolding the first tear tab 9 over the longitudinal side edge 12a of the packet 1 and rupturing the first tearing lines 8 along the longitudinally extending edge 24 of the absorbent article 2. In FIG. 19 each tear tab 9 is attached to the packet by the first tearing lines and by a portion of the first tear tab 9 being attached to the outside 5 of the backsheet 4 in the vicinity of the gripping means 31b. However, the first tear tab 9 may be removed by tearing two first tearing lines 8 along the longitudinally extending edge 24 of the absorbent article 2. Here, the second first tearing line may replace the above described attached part of the tear tab 9 close to the gripping means. In both examples, the gripping means may be a part of the tear tab 9 or may be attached to the tear tab 9.

Figure 20:
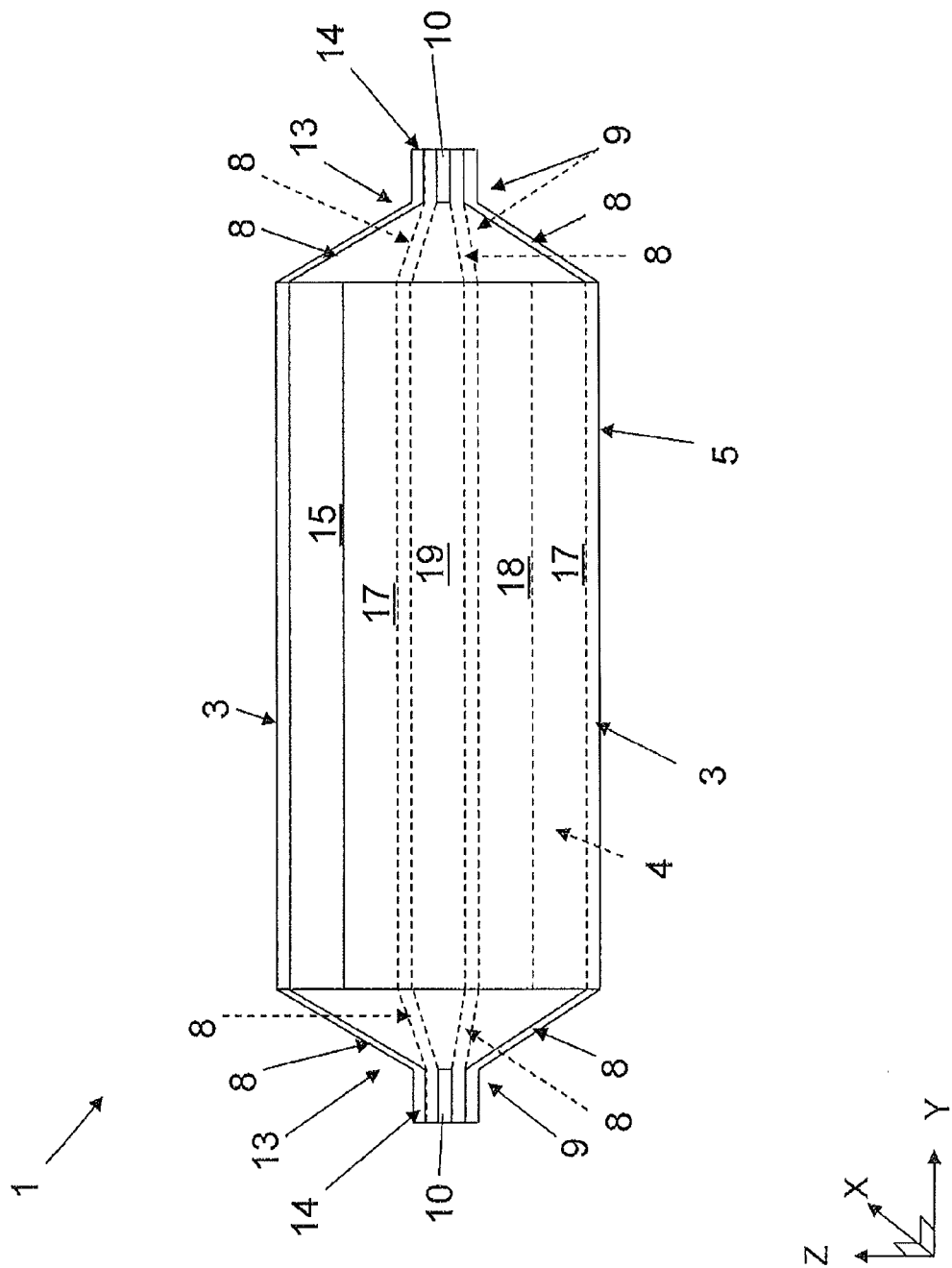
FIG. 20 schematically shows a front view of a packet according to the invention.

FIG. 20 schematically shows a front view of a packet according to the invention. FIG. 20 shows that the first tear tabs 9 are positioned in the central portion and the front portion and the rear portion. This solution can be used on the double folded, rolled or zig-zag folded absorbent article shown in any one of FIGS. 12-14.

Figure 21:
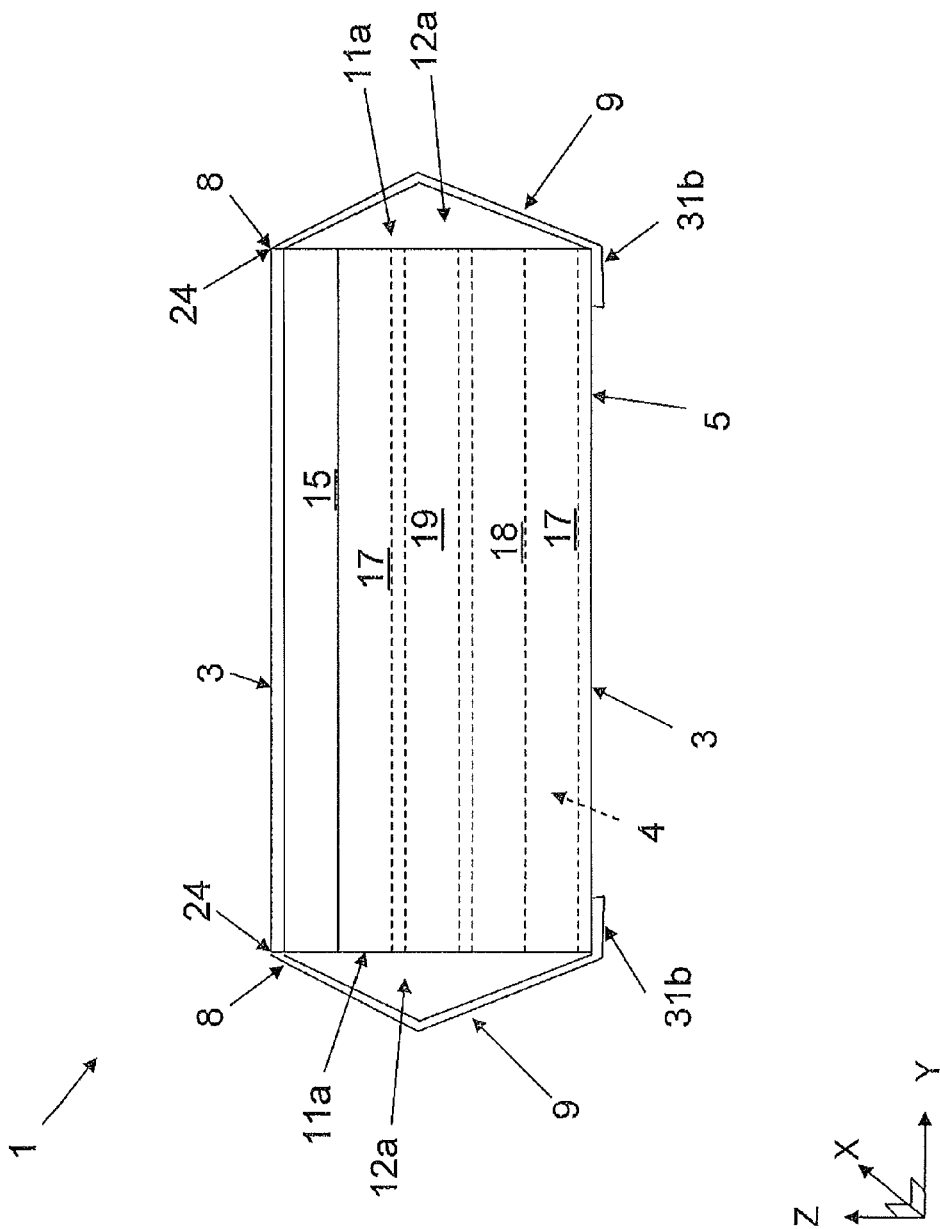
FIG. 21 schematically shows a front view of a packet according to the invention.

FIG. 21 schematically shows a front view of a packet according to the invention. FIG. 21 shows that the first tear tabs 9 are positioned in the front portion or the rear portion and are folded over the longitudinally extending side edge 12*a* of the packet 1. This solution can be used on the double folded, rolled or zig-zag folded absorbent article shown in any one of FIGS. 12-14.

The first tear tabs 9 can be removed by gripping a gripping means 31*b* for unfolding the first tear tab 9 over the longitudinal side edge 12*a* of the packet 1 and rupturing the first tearing lines 8 along the longitudinally extending edge 24 of the absorbent article 2. In FIG. 21 each tear tab 9 is attached to the packet by the first tearing lines and by a portion of the first tear tab 9 being attached to the outside 5 of the backsheet 4 in the vicinity of the gripping means 31*b*. However, the first tear tab 9 may be removed by tearing two first tearing lines 8 along the longitudinally extending edge 24 of the absorbent article 2. Here, the second first tearing line may replace the above described attached part of the tear tab 9 close to the gripping means. In both examples, the gripping means may be a part of the tear tab 9 or may be attached to the tear tab 9.

Figure 22:
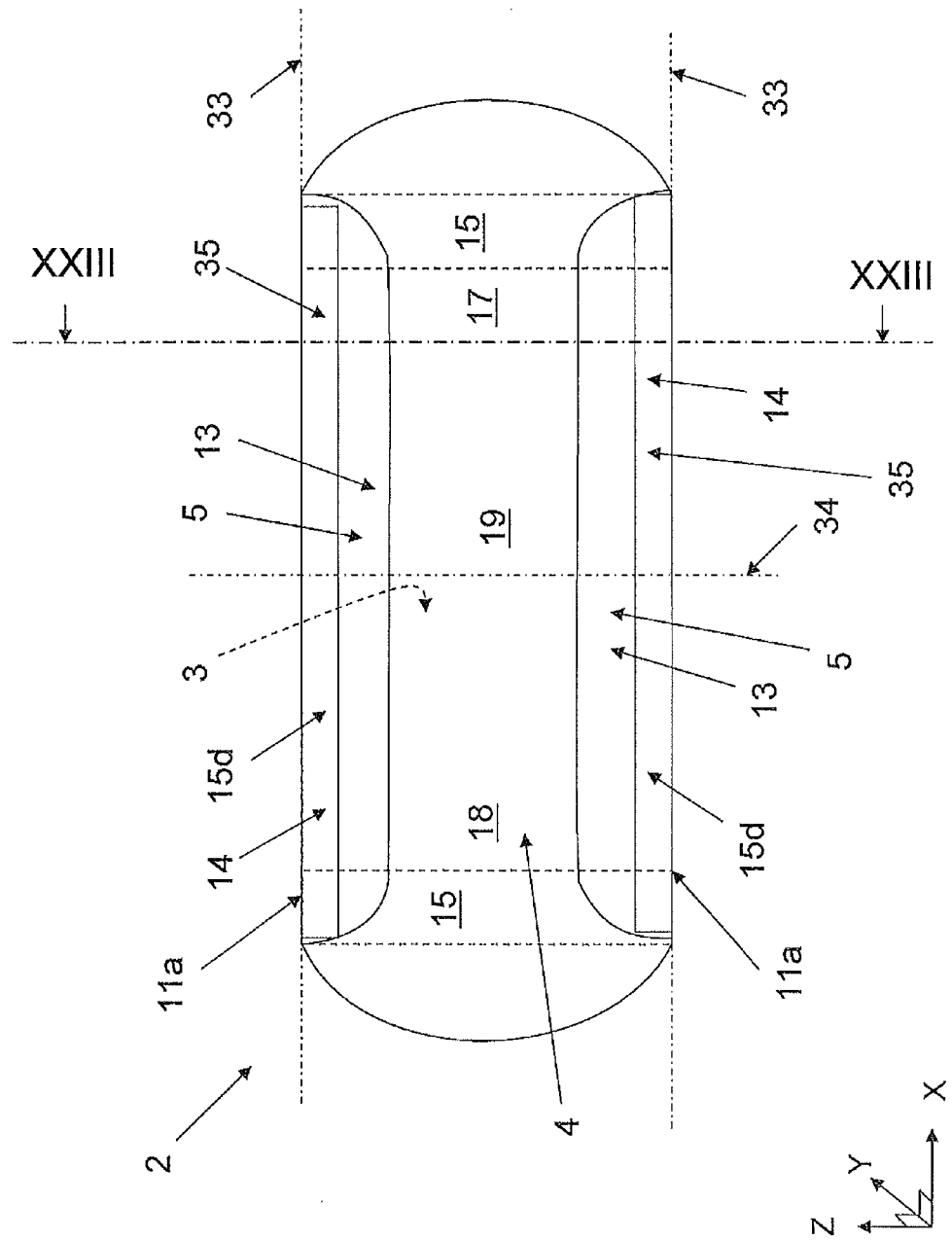
FIG. 22 schematically shows a top view of an absorbent article according to a fifth embodiment of the invention FIG. 23 schematically shows a cross-section along line XXIII in FIG. 22 according to a first example of the fifth embodiment, FIG. 24 schematically shows a cross-section along line XXIII in FIG. 22 according to a second example of the fifth embodiment.

FIG. 22 schematically shows a top view of an absorbent article according to a fifth embodiment of the invention. As mentioned in connection to FIGS. 1-21, the absorbent article 2 comprises, in its unfolded position, the longitudinal direction X and the lateral direction Y perpendicular to the longitudinal direction X and the thickness direction Z perpendicular to the plane described by the longitudinal direction X and the lateral direction X. The absorbent article 2 comprises, in the longitudinal direction X, the front portion 17, the rear portion 18 and the central portion 19 therebetween.

In FIG. 22 the longitudinally extending edge portions 13 are folded over longitudinally extending folding lines 33 and over the absorbent body 4. The absorbent article 2 is then folded over laterally extending folding lines 34 according to any one of FIGS. 2, 12, 13, 14, 23, 24 and 25. The folding lines 33, 34 may appear physically in the absorbent article 2 as weakened portions or creases or the like, but may also appear only in the drawings as an aid in describing the invention.

In FIG. 22 the fastening means 15 comprises fourth fastening means 15*d* positioned on the outside 5 of the backsheet 3 on the folded longitudinally extending edge portions 13. The fourth fastening means 15*d* may extend over the entire folded longitudinally extending edge portions 13 or only a part of the folded longitudinally extending edge portions 13. However, the fourth fastening means 15*d* shall extend in the longitudinal direction X when the absorbent article 2 is folded into the packet 1 for sealing the longitudinally extending side portions 11*a* of the packet 1. The fourth fastening means 15*d* are thus comprised in the first sealed portions 14 for sealing the longitudinally extending side portions 11*a* of the packet 1. Here "the fourth fastening means" may replace "the first sealing means" described in FIGS. 1-21 and may have all the properties described for the first sealing means, i.e. being separable or detachable from the backsheet. Hence, the fourth fastening means 15*d* form openable first sealed portions 14.

The packet 1 can be opened by breaking the bond in the fourth fastening means 15*d* for the fourth fastening means 15*d* to be used for attachment in the undergarment when the absorbent article 2 is in its unfolded position.

If the fourth fastening means 15*d* extend over the entire longitudinally extending edge portions 13, the fourth fastening means 15*d* will be attached to itself after the absorbent article has been folded into the packet 1. Hence, "breaking the bond in the fourth fastening means" could mean that the fourth fastening means 15*d* are separated into its original parts by breaking the bonds between the attachment surfaces 35 in the fourth fastening means 15*d*.

If the fourth fastening means 15*d* extend only partly over the longitudinally extending edge portions 13, the attachment surface 35 of the fourth fastening means 15*d* will be attached to the outside 5 of the backsheet 3 in the longitudinally extending edge portion 13 after the absorbent article 2 has been folded into the packet 1. Hence, "breaking the bond in the fourth fastening means" could mean that the fourth fastening means 15*d* are separated into two parts each having an attachment surface 35 that can be used for attachment in the undergarment when the absorbent article 2 is in its unfolded position.

If the fourth fastening means 15*d* extend only partly over the longitudinally extending edge portions 13, the attachment surface 35 of the fourth fastening means 15*d* will be attached to the outside of the backsheet in the longitudinally extending edge portion after the absorbent article 2 has been folded into the packet 1. Hence, "breaking the bond in the fourth fastening means" could mean that the packet 1 can be opened by breaking the bond between the attachment surface 35 in the fourth fastening means 15*d* and the backsheet so that the attachment surface 35 of the fourth fastening means 15*d* can be used for attachment in the undergarment when the absorbent article 2 is in its unfolded position.

One advantage of this embodiment is that the opening of the packet by breaking of the bond gives no waste products.

FIG. 22 shows one laterally extending folding line 34 positioned in such a way that the absorbent article is folded once over itself, i.e. double folded. This is also shown also in FIG. 24. However, if the absorbent article 2 is folded according to any of the embodiments described in connection to FIGS. 2, 12, 13 and 14 the fastening means 15 may comprise first and second fastening means 15*b* in addition to the fourth fastening means.

The folded longitudinally extending edge portions 13 may comprise a part of the absorbent body in the fold or may comprise only the backsheet material. The folded longitudinally extending edge portions 13 may comprise such flaps (see FIG. 24), comprising third fastening means, that has been described in connection to FIGS. 1-21.

Figure 23:
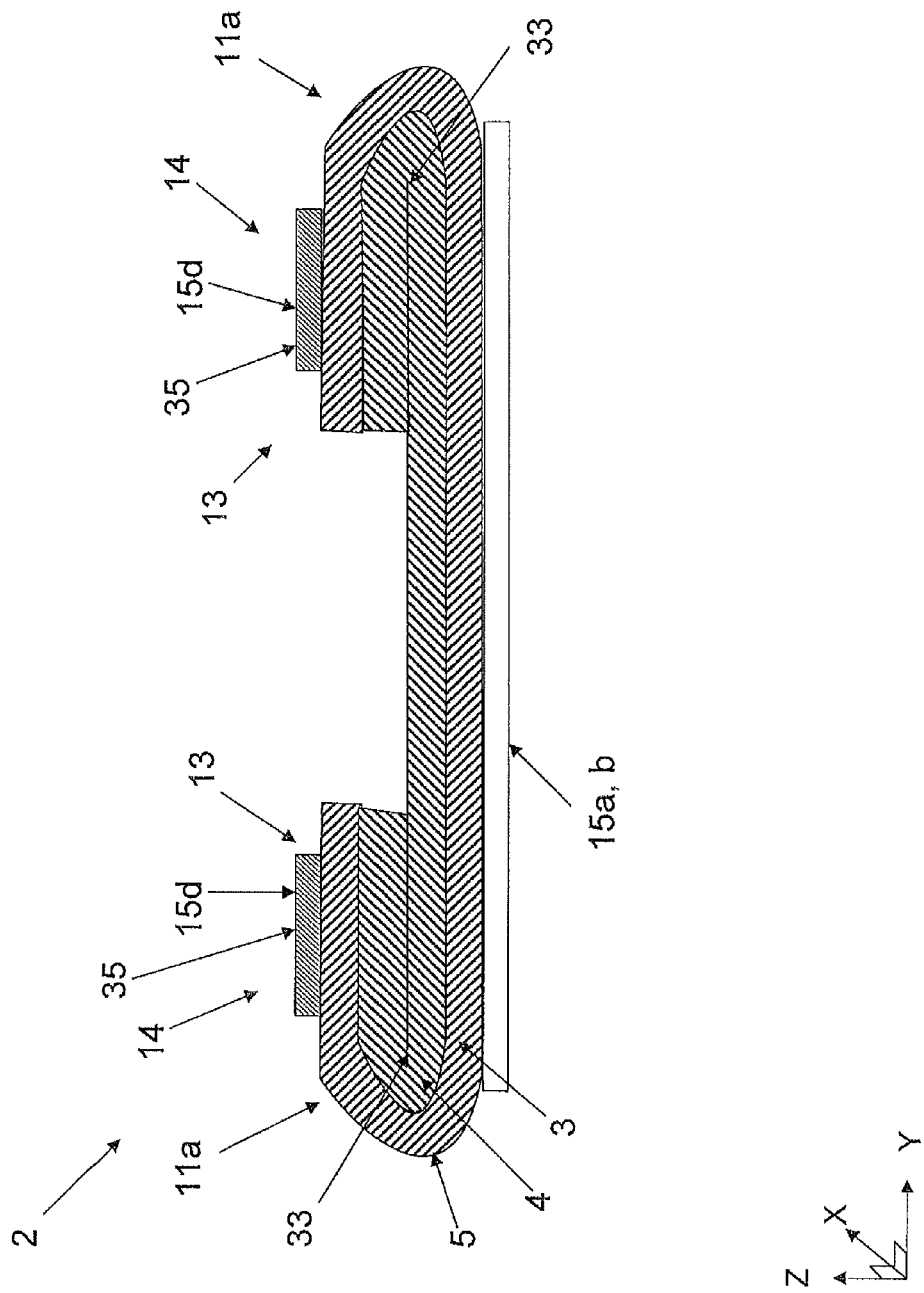

FIG. 23 schematically shows a cross-section along line XXIII in FIG. 22 according to a first example of the fifth embodiment. The folded longitudinally extending edge portions 13 comprises a part of the absorbent body in the fold and the fourth fastening means are positioned on the longitudinally extending edge portions 13.

Figure 24:
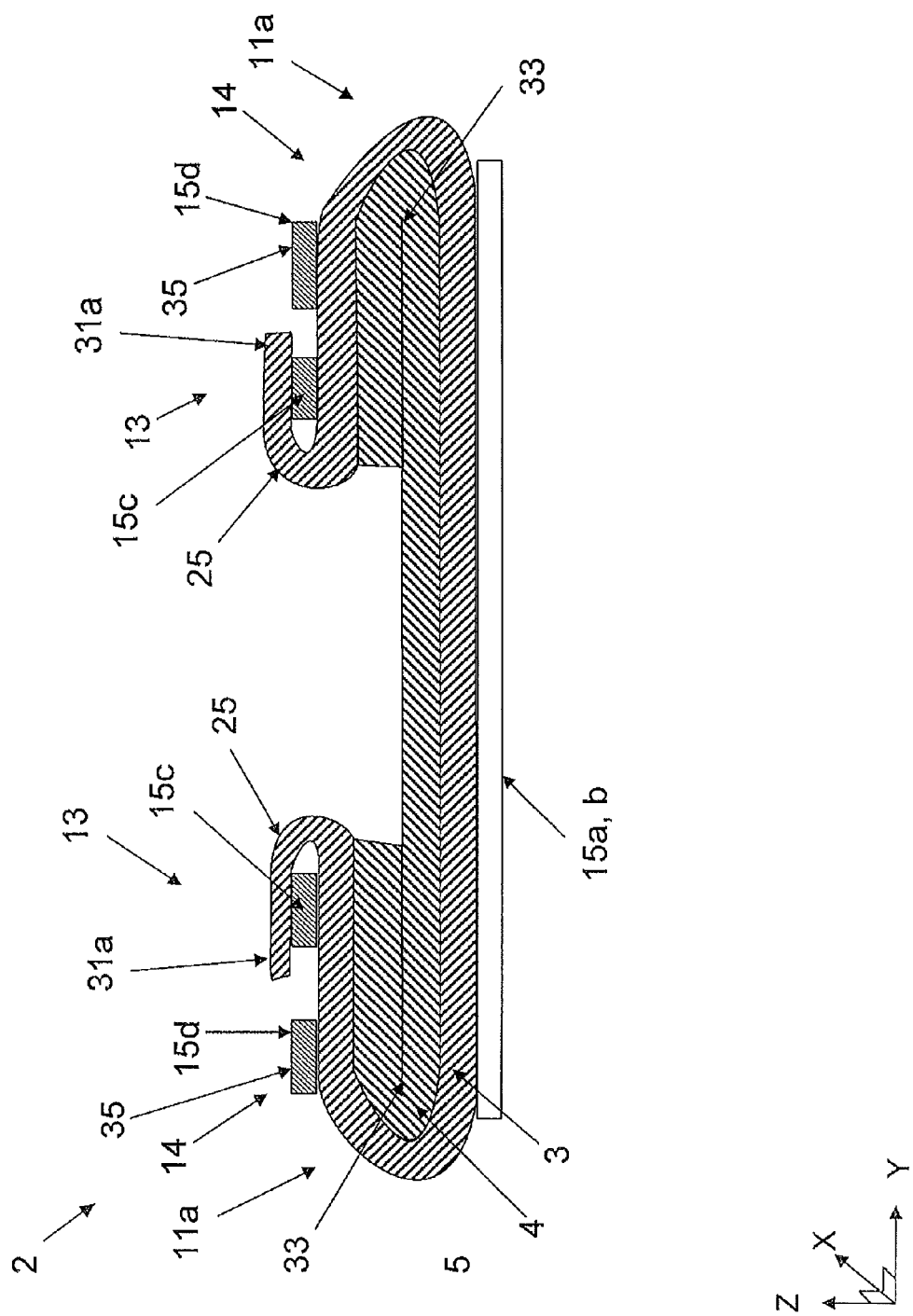

FIG. 24 schematically shows a cross-section along line XXIII in FIG. 22 according to a second example of the fifth embodiment. The second example is identical to the first example, but with the difference that the folded longitudinally extending edge portions 13 comprise flaps 25. The flaps 25 have been double folded, i.e. folded over themselves, in such a way that the third fastening means 15*c* have been hidden within the crease created by the double folded the flap. The reason for covering the third fastening means 15*c* is to avoid that the third fastening means becomes attached to the absorbent body when the packet is formed. This could be the case when the flaps 25, in its folded position, extend laterally towards each other in such a way that the third fastening means 15*c* cannot be attached to the outside 5 of the backsheet 3 in the folded longitudinally extending edge portions 13. However, the third fastening means 15*c* does not have to be double folded if the third fastening means 15*c* can be attached or lie against the outside 5 of the backsheet 3 in the folded longitudinally extending edge portions 13

FIG. 24 shows that the fourth fastening means 15d does not extend in the lateral direction so that the fourth fastening means 15d comes into contact with the folded flaps. The packet can then be opened by breaking the bonds in the fourth fastening means and the flaps can be unfolded by breaking the bonds in the third fastening means 15c. Here "breaking the bonds of the third fastening means" refers to the same possibilities as described in connection of the definition of "breaking the bonds of the fourth fastening means 15d. The flaps 25 may comprise gripping means 31a for an easy unfolding of the flaps 25.

Figure 25:
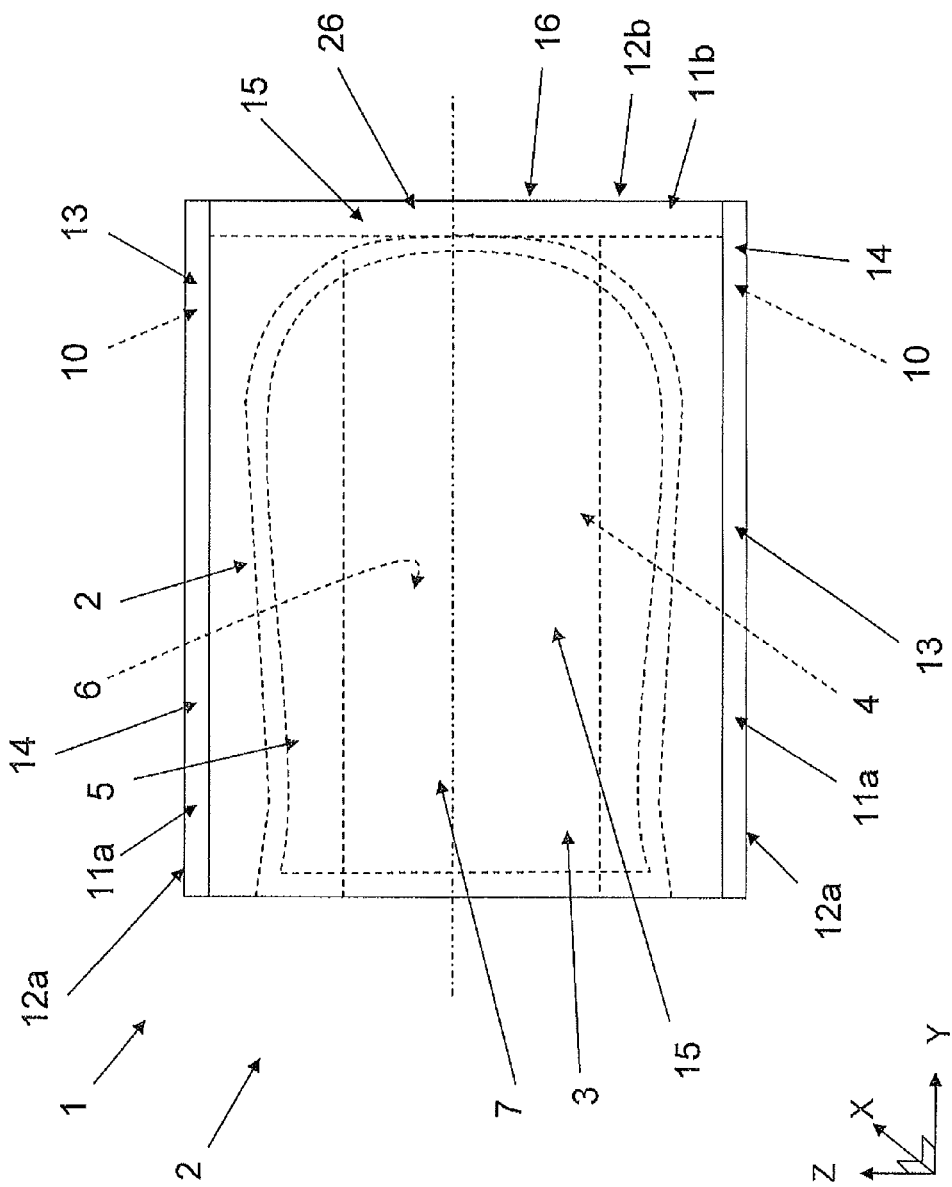
FIG. 25 shows an absorbent article according to any one of FIGS. 22-24 being folded into a packet 1.

FIG. 25 shows an absorbent article according to any one of FIGS. 22-24 being folded into a packet 1. In addition to what has been described in connection to FIGS. 22-24, the packet 1 is sealed along the laterally extending side edge 12b of the packet 1. Depending on how the absorbent article is folded into the packet 1, i.e. according to any of the possibilities described in connection to any one of or a combination of FIGS. 1-24, the seal either comprises a laterally extending openable second sealed portion 16 comprising first and/or second fastening means 15a, 15b or removable second tear tabs 26. The latter is possible, for example, when the absorbent article 2 is double folded over a centrally positioned folding line such that the fourth fastening means 15d is comprised in the first sealed portion.

Figure 26:
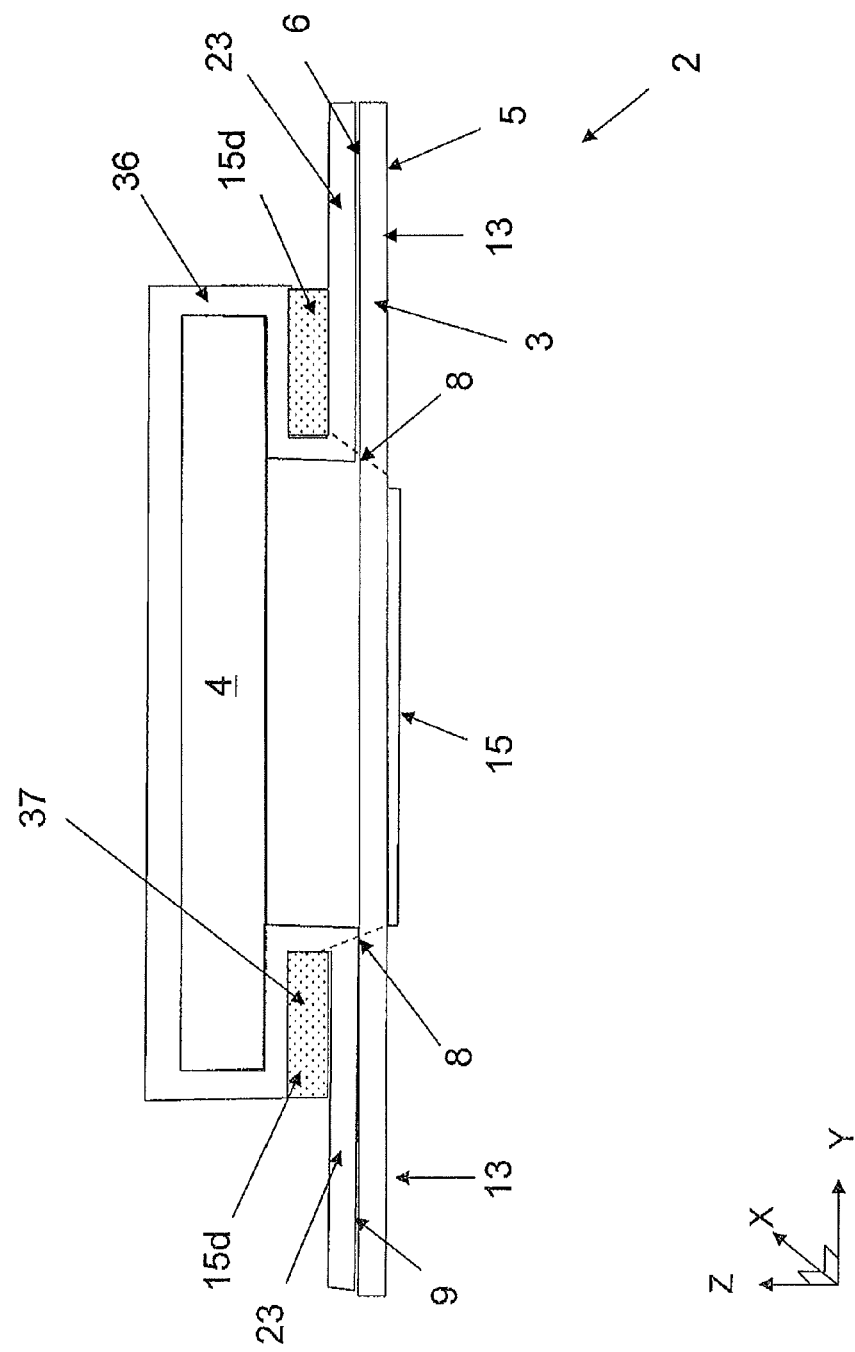
FIG. 26 schematically shows a side view of an absorbent article according to a sixth embodiment of the invention.

FIG. 26 schematically shows a side view of an absorbent article according to a sixth embodiment of the invention. The embodiment shown in FIG. 26 can be combined with any one of the embodiments described in connection to FIGS. 1-21 with regarding to the folding possibilities for forming the packet.

In FIG. 26 the absorbent article comprises a topsheet 36, a backsheet 3 and an absorbent body 4 positioned therebetween. In FIG. 26 the topsheet 36 has been folded between the absorbent body 4 and the backsheet in order to create one crease 37 on each side of the absorbent article 2. In FIG. 26 each crease 37 has an extension along the longitudinally extending edge portions 13. The crease 37 comprises fastening means 15d and the previously described tearing line 8 extends through both the topsheet 36 and the backsheet 3. In FIG. 26 the first tear tabs 9 comprise the backsheet 3 and the topsheet 36, but in another embodiment the fastening means 15d may be positioned between the backsheet and the topsheet 36 when the topsheet has been folded over a part of the backsheet. In both cases the fastening means 15d is revealed by removing the first tear tabs 9. In FIG. 26 the tearing line 8 is thus positioned such that when a user removes the first tear tabs 9 the fastening means 15d is at least partly revealed for use against the undergarment.

FIG. 27 schematically shows a side view of an absorbent article according to a seventh embodiment of the invention. The embodiment shown in FIG. 27 can be combined with any one of the embodiments described in connection to FIGS. 1-21 with regarding to the folding possibilities for forming the packet.

In FIG. 27 the absorbent article comprises a topsheet 36, a backsheet 3 and an absorbent body 4 positioned therebetween. In FIG. 27 the backsheet 3 has been folded twice in order to create one crease 38 on each side of the absorbent article 2. In FIG. 27 each crease 38 has an extension along the longitudinally extending edge portions 13. The crease 38 comprises fastening means 15e and the previously described tearing line 8 extends through the backsheet 3. In FIG. 27 the first tear tabs 9 comprise the backsheet 3 and the fastening means 15d is revealed by removing the first tear tabs 9. In FIG. 26 the tearing line 8 is thus positioned such that when a user removes the first tear tabs 9 the fastening means 15d is at least partly revealed for use against the undergarment.

FIG. 28 schematically shows a side view of an absorbent article according to an eight embodiment of the invention. The embodiment shown in FIG. 27 can be combined with any one of the embodiments described in connection to FIGS. 1-21 with regarding to the folding possibilities for forming the packet. FIG. 28 is identical to FIG. 27 but with the exception that the position of the tearing line 8 has been altered. In FIG. 28 the tearing line 8 is positioned such that the backsheet 3 must be unfolded in order to reveal the fastening means 15e. Hence, the tearing line 8 is stronger than the adhesive force between fastening means 15e and that part of the backsheet 3 that has been folded in order to create the crease 38. The cohesive force between the fastening means 15e and that part of the backsheet 3 positioned in connection to the absorbent body 4 must however be higher than between the fastening means 15e and the folded part of the backsheet 3 in order for the fastening means 15e to remain in position for use against the undergarment. In order to create different cohesive force between the backsheet 3 and the fastening means, the outside 5 of backsheet can be treated with different methods in order to change the cohesive properties against the fastening means 15e. For example, the folded part of the backsheet 3 may be treated with silicone or any other suitable substance that lowers the cohesive force or the other part of the backsheet may be treated with a cohesive enhancing method.

When the creased part of the backsheet has been unfolded, the first tear tabs 9 are removed and that part of the backsheet that extends in a lateral direction in the longitudinally extending edge portions 13 may serve as flaps after the fastening means 15e have been revealed.

The invention is not limited to the embodiments described in the drawings, but may be amended within the scope of the claims. For example, the outside of the backsheet may partly or wholly be treated to give the outside of the backsheet specific properties in selected areas. For example, the specific properties can give high friction between the backsheet and the undergarment. The treatment of the backsheet can be made by coating the backsheet or by attaching a film to the outside of the backsheet.

Furthermore, the fastening means may in the form of an adhesive have different bonding properties in different zones and may have different cohesive properties. The adhesive can be arranged in one or more continuous lines being straight or curved and/or the adhesive can be arranged as a number of dots having any suitable geometrical shape, for example round, oval, polygonal, rectangular, square, etc.

The absorbent article may comprise flaps/wings for attachment against an outside or an inside of an undergarment. The flaps may be part of the backsheet or attached to the absorbent article. The flaps may comprise different materials that make them possible to form into a desired shape by the user pulling the flap in a desired direction. The flap may thus be elastic and may be plastically deformable and may comprise reinforced regions and/or reinforcing means for aid in shaping the flap.

The backsheet may be breathable, i.e. allow diffusion of moist air to the ambient air, and may comprise different zones with different degree of breathability. The so called wetting spot, i.e. that part of the absorbent article that receives the most liquid, may be formed from a non-breathable material, or a less breathable material, while adjacent/surrounding/partly surrounding materials may be highly breathable. One example of non-breathable material is plastic and one example of breathable material is nonwoven. The invention is not limited to these materials, but essentially any material known from prior art can be used.

The invention claimed is:

1. An absorbent article comprising:
   a backsheet having an outside, an inside and two longitudinally extending edge portions;
   an absorbent body positioned on the inside of the backsheet;
   a fastening device positioned on the outside of the backsheet for fastening the absorbent article to an undergarment when the absorbent article is in an unfolded position;
   wherein the absorbent article in a folded position is folded into a packet in such a way that:
      at least a part of the outside of the backsheet makes up an exterior surface of the packet,
      the fastening device is positioned inside the packet, and each longitudinally extending edge portion is folded over itself at least once and attached to itself forming openable first sealed portions for sealing longitudinally extending side portions of the packet; and
   wherein the fastening device is in contact only with the outside of the backsheet when the absorbent article is in the folded position; and
   wherein the fastening device is arranged to seal continuously across an entirety of a laterally extending side portion of the packet in a folded position thereby forming a second sealed portion.

2. The absorbent article according to claim 1, wherein the fastening device comprises an attachment surface facing away from the outside of the absorbent article when the absorbent article is in the unfolded position, wherein the attachment surface is arranged for attachment to the undergarment when the absorbent article is in the unfolded position, wherein the attachment surface is in contact only with the outside of the backsheet when the absorbent article is in the folded position.

3. The absorbent article according to claim 1, wherein the fastening device comprises at least a first fastening device and a second fastening device, wherein the first fastening device is attached to the second fastening device or the attachment surface of the first fastening device is attached to the outside of the backsheet and the second fastening device is attached to the outside of the backsheet.

4. The absorbent article according to claim 1, wherein the second sealed portion is separable for opening the packet.

5. The absorbent article according to claim 1, wherein the absorbent article in its unfolded position has a longitudinal direction and a lateral direction perpendicular to the longitudinal direction and a thickness direction perpendicular to the plane described by the longitudinal direction and the lateral direction, wherein the absorbent article in the longitudinal direction comprises a front portion, a rear portion and a central portion therebetween, wherein the absorbent article is folded in such a way that the absorbent body in the front portion faces a part of the absorbent body in the central portion and in such a way that the absorbent body in the rear portion faces a part of the absorbent body in the central portion, and in such a way that at least a part of the outside of the backsheet in the front portion is interconnected via the fastening device to at least a part of the outside of the backsheet in the rear portion.

6. The absorbent article according to claim 1, wherein the absorbent article in its unfolded position has a longitudinal direction and a lateral direction perpendicular to the longitudinal direction and a thickness direction perpendicular to the plane described by the longitudinal direction and the lateral direction, wherein the absorbent article in the longitudinal direction comprises a front portion, a rear portion and a central portion therebetween, wherein the absorbent article is folded in such a way that the front portion is double folded in such a way that the absorbent body faces itself and in such a way that the rear portion is rolled in a direction towards the central portion, and in such a way that at least a part of the outside of the backsheet in the front portion is interconnected via the fastening device to at least a part of the outside of the backsheet in the rear portion.

7. The absorbent article according to claim 1, wherein the absorbent article in its unfolded position has a longitudinal direction and a lateral direction perpendicular to the longitudinal direction and a thickness direction perpendicular to the plane described by the longitudinal direction and the lateral direction, wherein the absorbent article in the longitudinal direction comprises a front portion, a rear portion and a central portion therebetween, wherein the absorbent article is folded in such a way that the rear portion is double folded in such a way that the absorbent body faces itself and in such a way that the front portion is rolled in a direction towards the central portion, and in such a way that at least a part of the outside of the backsheet in the front portion is interconnected via the fastening device to at least a part of the outside of the backsheet in the rear portion.

8. The absorbent article according to claim 1, wherein the absorbent article in its unfolded position has a longitudinal direction and a lateral direction perpendicular to the longitudinal direction and a thickness direction perpendicular to the plane described by the longitudinal direction and the lateral direction, wherein the absorbent article in the longitudinal direction comprises a front portion, a rear portion and a central portion therebetween, wherein the absorbent article is rolled in a direction from the front portion towards the central portion and from the rear portion to the central portion in such a way that at least a part of the outside of the backsheet of the front portion is interconnected via the fastening device to at least a part of the outside) of the backsheet of the rear portion.

9. The absorbent article according to claim 1, wherein the first sealed portions are separable, for opening the packet.

10. The absorbent article according to claim 1, wherein the longitudinally extending edge portions are folded over longitudinally extending folding lines for forming the first sealed portions.

11. The absorbent article according to claim 10, wherein the fastening device comprises a fourth fastening device positioned on the outside of the backsheet on the folded longitudinally extending edge portions.

12. The absorbent article according to claim 1, wherein the fastening device comprises an adhesive.

13. An absorbent article comprising:
   a backsheet having an outside, an inside and two longitudinally extending edge portions;
   an absorbent body positioned on the inside of the backsheet;
   a fastening device positioned on the outside of the backsheet for fastening the absorbent article to an undergarment when the absorbent article is in an unfolded position;
   the backsheet comprises fastening flaps extending, when the absorbent article is in the unfolded position, along each of the longitudinally extending edge portions and extending in the lateral direction in a direction away from the absorbent body;
   wherein the absorbent article in a folded position is folded into a packet in such a way that:
      at least a part of the outside of the backsheet makes up an exterior surface of the packet,
      the fastening device is positioned inside the packet, and each longitudinally extending edge portion is folded over itself at least once and attached to itself forming removable first sealed portions for sealing longitudinally extending side portions of the packet; and wherein the flaps are comprised in the first sealed portions and wherein separation of the removable first sealed portions from the backsheet of the packet when the absorbent article is in its folded position is arranged to form the shape of the flaps.

14. The absorbent article according to claim 13, wherein the fastening device is in contact only with the outside of the backsheet when the absorbent article is in the folded position.

15. The absorbent article according to claim 13, wherein the fastening device comprises an attachment surface facing away from the outside of the absorbent article when the absorbent article is in the unfolded position, wherein the attachment surface is arranged for attachment in the undergarment when the absorbent article is in the unfolded position, wherein the attachment surface is in contact only with the outside of the backsheet when the absorbent article is in the folded position.

16. The absorbent article according to claim 15, wherein the fastening device comprises at least a first fastening device and a second fastening device, wherein the first fastening device is attached to the second fastening device or the attachment surface of the first fastening device is attached to the outside of the backsheet and the second fastening device is attached to the outside of the backsheet.

17. The absorbent article according to claim 13, wherein the fastening device is arranged to seal a laterally extending side portion of the packet in a folded position thereby forming a second sealed portion.

18. The absorbent article according to claim 17, wherein the second sealed portion is separable for opening the packet.

19. The absorbent article according to claim 13, wherein the absorbent article in its unfolded position has a longitudinal direction and a lateral direction perpendicular to the longitudinal direction and a thickness direction perpendicular to the plane described by the longitudinal direction and the lateral direction, wherein the absorbent article in the longitudinal direction comprises a front portion, a rear portion and a central portion therebetween, wherein the absorbent article is folded in such a way that the absorbent body in the front portion faces a part of the absorbent body in the central portion and in such a way that the absorbent body in the rear portion faces a part of the absorbent body in the central portion, and in such a way that at least a part of the outside of the backsheet in the front portion is interconnected via the fastening device to at least a part of the outside of the backsheet in the rear portion.

20. The absorbent article according to claim 13, wherein the absorbent article in its unfolded position has a longitudinal direction and a lateral direction perpendicular to the longitudinal direction and a thickness direction perpendicular to the plane described by the longitudinal direction and the lateral direction, wherein the absorbent article in the longitudinal direction comprises a front portion, a rear portion and a central portion therebetween, wherein the absorbent article is folded in such a way that the front portion is double folded in such a way that the absorbent body faces itself and in such a way that the rear portion is rolled in a direction towards the central portion, and in such a way that at least a part of the outside of the backsheet in the front portion is interconnected via the fastening device to at least a part of the outside of the backsheet in the rear portion.

21. The absorbent article according to claim 13, wherein the absorbent article in its unfolded position has a longitudinal direction and a lateral direction perpendicular to the longitudinal direction and a thickness direction perpendicular to the plane described by the longitudinal direction and the lateral direction, wherein the absorbent article in the longitudinal direction comprises a front portion, a rear portion and a central portion therebetween, wherein the absorbent article is folded in such a way that the rear portion is double folded in such a way that the absorbent body faces itself and in such a way that the front portion is rolled in a direction towards the central portion, and in such a way that at least a part of the outside of the backsheet in the front portion is interconnected via the fastening device to at least a part of the outside of the backsheet in the rear portion.

22. The absorbent article according to claim 13, wherein the absorbent article in its unfolded position has a longitudinal direction and a lateral direction perpendicular to the longitudinal direction and a thickness direction perpendicular to the plane described by the longitudinal direction and the lateral direction, wherein the absorbent article in the longitudinal direction comprises a front portion, a rear portion and a central portion therebetween, wherein the absorbent article is rolled in a direction from the front portion towards the central portion and from the rear portion to the central portion in such a way that at least a part of the outside of the backsheet of the front portion is interconnected via the fastening device to at least a part of the outside of the backsheet of the rear portion.

23. The absorbent article according to claim 13, wherein the first sealed portions comprise first tearing lines for separation of first tear tabs from the backsheet from the packet when the absorbent article is in its folded position, or wherein the first sealed portions are separable, for opening the packet.

24. The absorbent article according to claim 13, wherein the longitudinally extending edge portions are folded over longitudinally extending folding lines for forming the first sealed portions.

25. The absorbent article according to claim 24, wherein the fastening device comprises a fourth fastening device positioned on the outside of the backsheet on the folded longitudinally extending edge portions.

26. The absorbent article according to claim 13, wherein the flaps are attached to the backsheet or are a part of the backsheet material.

27. The absorbent article according to claim 13, wherein the separation of the removable first sealed portions from the backsheet of the packet when the absorbent article is in its folded position is arranged to form the shape of the longitudinally extending edges of the flaps.

28. An absorbent article comprising:
a backsheet having an outside, an inside and two longitudinally extending edge portions;
an absorbent body positioned on the inside of the backsheet;
a fastening device positioned on the outside of the backsheet for fastening the absorbent article to an undergarment when the absorbent article is in an unfolded position;
wherein the absorbent article in a folded position is folded into a packet in such a way that:
at least a part of the outside of the backsheet makes up an exterior surface of the packet,
the fastening device is positioned inside the packet, and
each longitudinally extending edge portion is folded over itself at least once and attached to itself forming openable first sealed portions for sealing longitudinally extending side portions of the packet; and wherein the fastening device is in contact only with the outside of the backsheet when the absorbent article is in the folded position;

wherein the fastening device is arranged to seal a laterally extending side portion of the packet in a folded position thereby forming a second sealed portion; and wherein the absorbent article in its unfolded position has a longitudinal direction and a lateral direction perpendicular to the longitudinal direction and a thickness direction perpendicular to the plane described by the longitudinal direction and the lateral direction, wherein the absorbent article in the longitudinal direction comprises a front portion, a rear portion and a central portion therebetween, wherein the absorbent article is folded in such a way that the absorbent body in the front portion faces a part of the absorbent body in the central portion and in such a way that the absorbent body in the rear portion faces a part of the absorbent body in the central portion, and in such a way that at least a part of the outside of the backsheet in the central portion is interconnected via the fastening device to at least a part of the outside of the backsheet in another part of the central portion.

29. The absorbent article according to claim 28, wherein the backsheet comprises two laterally extending edge portions being folded over each other forming a third sealed portion for sealing a laterally extending side portion of the packet, wherein the third sealed portion comprises second tearing lines for separation of a second tear tab from the backsheet from the packet when the absorbent article is in its folded position, or wherein the third sealed portions are separable, for opening the packet.

30. An absorbent article comprising:
a backsheet having an outside, an inside and two longitudinally extending edge portions;
an absorbent body positioned on the inside of the backsheet;
a fastening device positioned on the outside of the backsheet for fastening the absorbent article to an undergarment when the absorbent article is in an unfolded position;
the backsheet comprises fastening flaps extending, when the absorbent article is in the unfolded position, along each of the longitudinally extending edge portions and extending in the lateral direction in a direction away from the absorbent body;

wherein the absorbent article in a folded position is folded into a packet in such a way that:
at least a part of the outside of the backsheet makes up an exterior surface of the packet,
the fastening device is positioned inside the packet, and
each longitudinally extending edge portion is folded over itself at least once and attached to itself forming removable first sealed portions for sealing longitudinally extending side portions of the packet; and wherein the flaps are comprised in the first sealed portions and wherein separation of the first tear tabs from the backsheet of the packet when the absorbent article is in its folded position is arranged to form the shape of the flaps;

wherein the absorbent article in its unfolded position has a longitudinal direction and a lateral direction perpendicular to the longitudinal direction and a thickness direction perpendicular to the plane described by the longitudinal direction and the lateral direction, wherein the absorbent article in the longitudinal direction comprises a front portion, a rear portion and a central portion therebetween, wherein the absorbent article is folded in such a way that the absorbent body in the front portion faces a part of the absorbent body in the central portion and in such a way that the absorbent body in the rear portion faces a part of the absorbent body in the central portion, and in such a way that at least a part of the outside of the backsheet in the central portion is interconnected via the fastening device to at least a part of the outside of the backsheet in another part of the central portion.

31. The absorbent article according to claim 30, wherein the backsheet comprises two laterally extending edge portions being folded over each other forming a third sealed portion for sealing a laterally extending side portion of the packet, wherein the third sealed portion comprises second tearing lines for separation of a second tear tab from the backsheet from the packet when the absorbent article is in its folded position, or wherein the third sealed portions are separable, for opening the packet.

* * * * *